(12) United States Patent
Dejima

(10) Patent No.: US 10,398,291 B2
(45) Date of Patent: Sep. 3, 2019

(54) ENDOSCOPIC SURGICAL DEVICE AND OVERTUBE

(71) Applicant: FUJIFILM Corporation, Tokyo (JP)

(72) Inventor: Takumi Dejima, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 273 days.

(21) Appl. No.: 15/275,478

(22) Filed: Sep. 26, 2016

(65) Prior Publication Data

US 2017/0007102 A1    Jan. 12, 2017

Related U.S. Application Data

(63) Continuation of application No. PCT/JP2015/059351, filed on Mar. 26, 2015.
(Continued)

(51) Int. Cl.
*A61B 1/00* (2006.01)
*A61B 17/34* (2006.01)
(Continued)

(52) U.S. Cl.
CPC ........ *A61B 1/00135* (2013.01); *A61B 1/0014* (2013.01); *A61B 1/00018* (2013.01);
(Continued)

(58) Field of Classification Search
CPC ............ A61B 1/00135; A61B 1/00018; A61B 1/00154; A61B 1/05; A61B 1/0661;
(Continued)

(56) References Cited

U.S. PATENT DOCUMENTS 5,269,772 A * 12/1993 Wilk .................. A61B 1/00135
604/264
6,371,968 B1 * 4/2002 Kogasaka ........ A61B 17/00234
600/201
(Continued)

FOREIGN PATENT DOCUMENTS

EP        2163217       3/2010
JP     2006-087687      4/2006
(Continued)

OTHER PUBLICATIONS

"Written Opinion of the International Searching Authority (Form PCT/ISA/237)" of PCT/JP2015/059351, dated Jun. 23, 2015, pp. 1-8.
(Continued)

*Primary Examiner* — Ryan N Henderson
*Assistant Examiner* — Pamela F Wu
(74) *Attorney, Agent, or Firm* — JCIPRNET

(57) ABSTRACT

An overtube to be inserted into a body wall is provided with an endoscope insertion passage and a treatment tool insertion passage, the treatment tool insertion passage is provided parallel to a reference axis of the overtube, and the endoscope insertion passage is provided obliquely to the reference axis. A slider, which is engaged with the endoscope and the treatment tool inserted through the respective insertion passages and causes the endoscope and the treatment tool to interlock with each other and move forward and backward, is arranged inside the overtube so as to be movable in a forward-backward direction of the overtube. An endoscope engagement part engaged with the endoscope in the slider is movable in an upward-downward direction, and moves upward and downward along the position of the oblique endoscope insertion passage together with the movement of the slider in the forward-backward direction.

14 Claims, 31 Drawing Sheets

Related U.S. Application Data

(60) Provisional application No. 61/971,220, filed on Mar. 27, 2014.

(51) Int. Cl.
*A61B 1/05* (2006.01)
*A61B 1/06* (2006.01)
*A61B 1/018* (2006.01)

(52) U.S. Cl.
CPC ...... *A61B 1/00133* (2013.01); *A61B 1/00154* (2013.01); *A61B 1/018* (2013.01); *A61B 1/05* (2013.01); *A61B 1/0661* (2013.01); *A61B 17/3421* (2013.01); *A61B 2017/347* (2013.01); *A61B 2017/3445* (2013.01); *A61B 2017/3447* (2013.01); *A61B 2017/3466* (2013.01)

(58) Field of Classification Search
CPC ...... A61B 17/3421; A61B 2017/00738; A61B 2017/3445; A61B 2017/3447; A61B 2017/3466; A61B 2017/347; A61B 1/00131; A61B 1/00147; A61B 1/00151; A61B 1/00133; A61B 1/0014; A61B 1/018
USPC .......................................... 600/114, 121–125
See application file for complete search history.

(56) References Cited

U.S. PATENT DOCUMENTS

| | | | |
|---|---|---|---|
| 2005/0119525 A1* | 6/2005 | Takemoto | A61B 1/00154 600/114 |
| 2006/0069304 A1 | 3/2006 | Takemoto et al. | |
| 2010/0016659 A1 | 1/2010 | Weitzner | |
| 2010/0228094 A1* | 9/2010 | Ortiz | A61B 17/3423 600/205 |
| 2011/0071348 A1 | 3/2011 | Blanchard | |
| 2011/0166422 A1* | 7/2011 | Ross | A61B 1/00154 600/204 |
| 2011/0263937 A1 | 10/2011 | Korner et al. | |
| 2015/0080650 A1 | 3/2015 | Dejima et al. | |

FOREIGN PATENT DOCUMENTS

| | | |
|---|---|---|
| JP | 2007-050269 | 3/2007 |
| JP | 2011-520492 | 7/2011 |
| JP | 2011-224376 | 11/2011 |
| JP | 2011-528576 | 11/2011 |
| WO | 2013/176167 | 1/2016 |

OTHER PUBLICATIONS

"Search Report of Europe Counterpart Application", dated Feb. 27, 2017, p. 1-8.

* cited by examiner

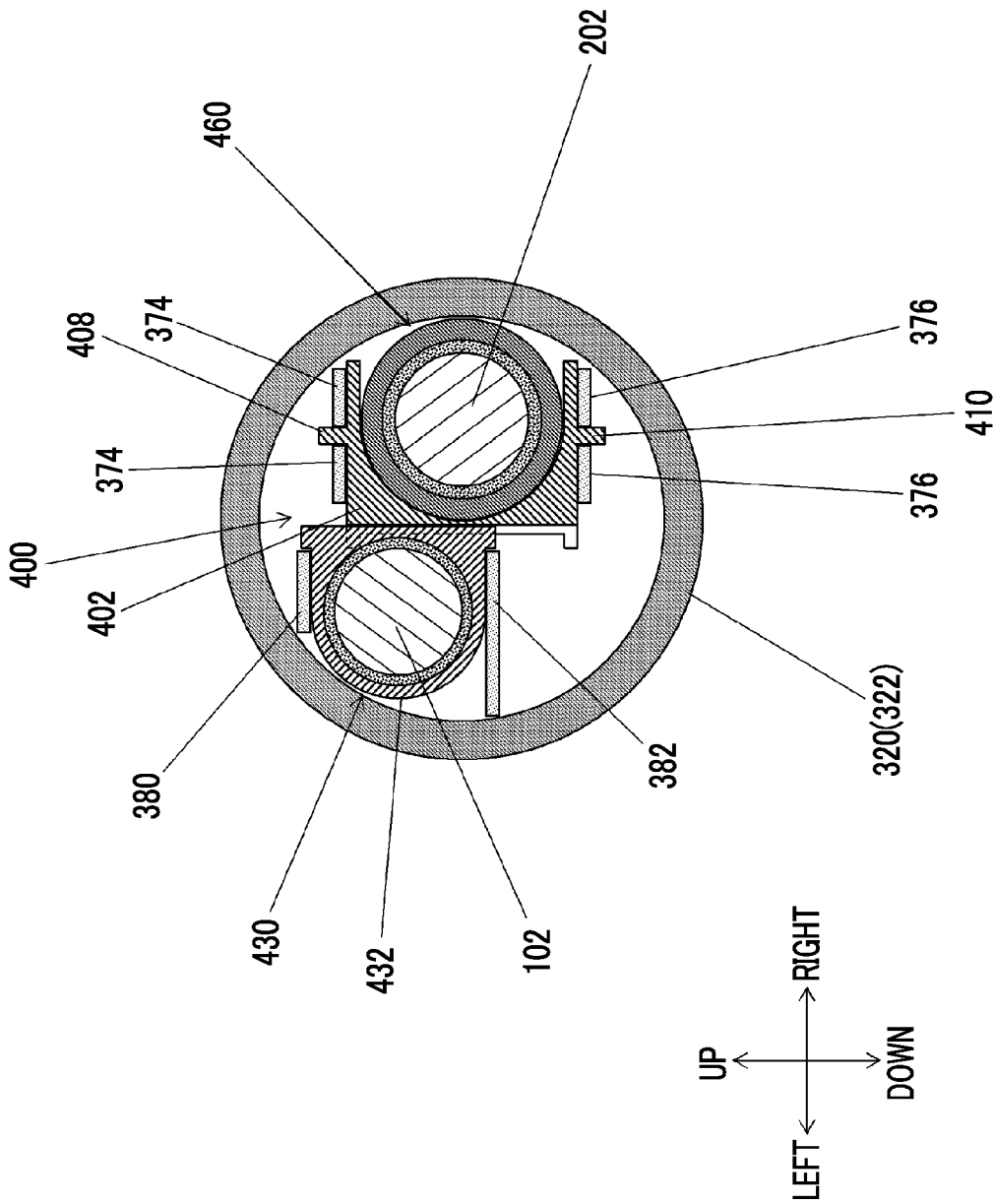

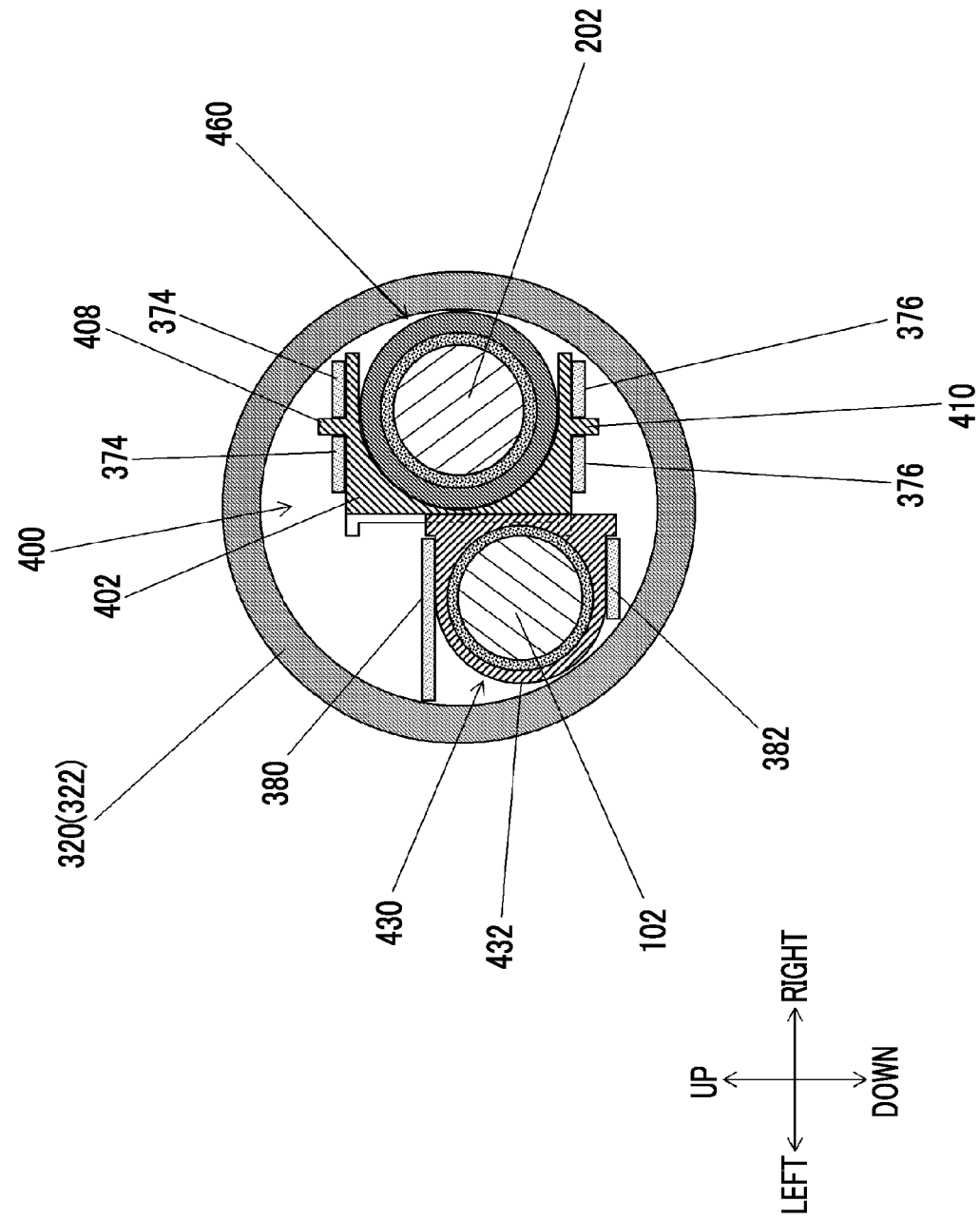

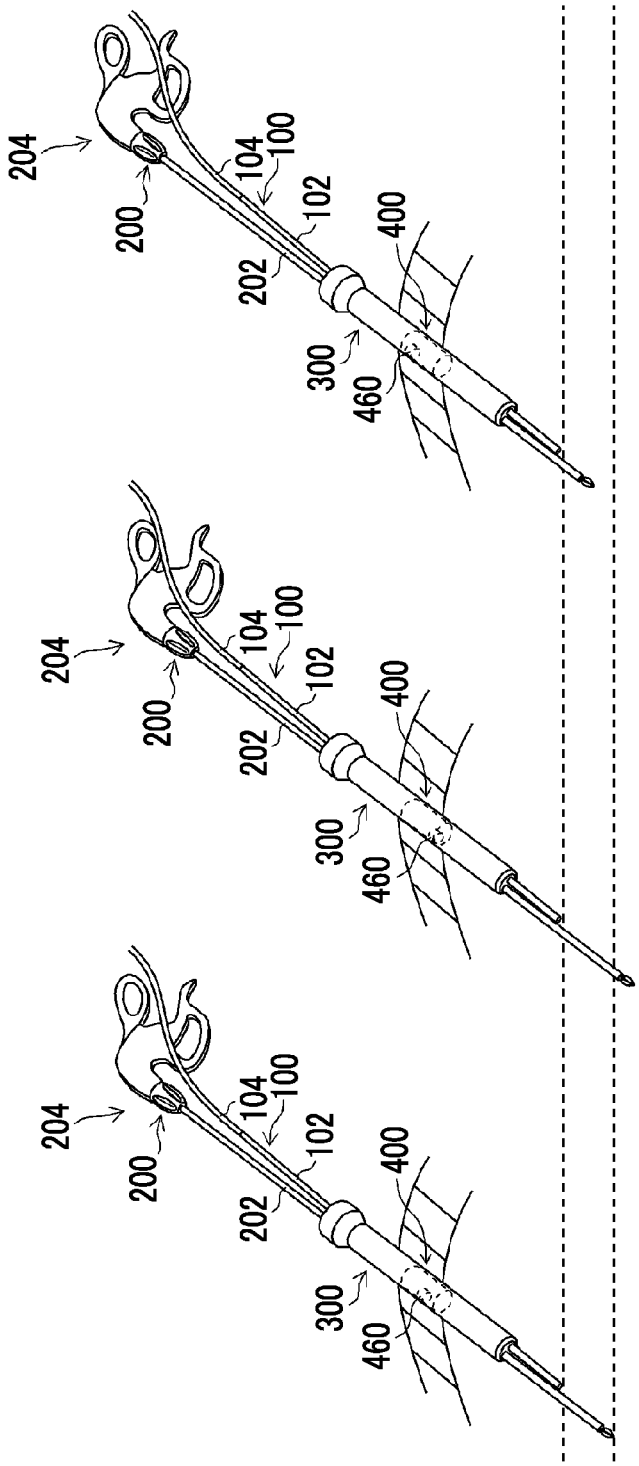

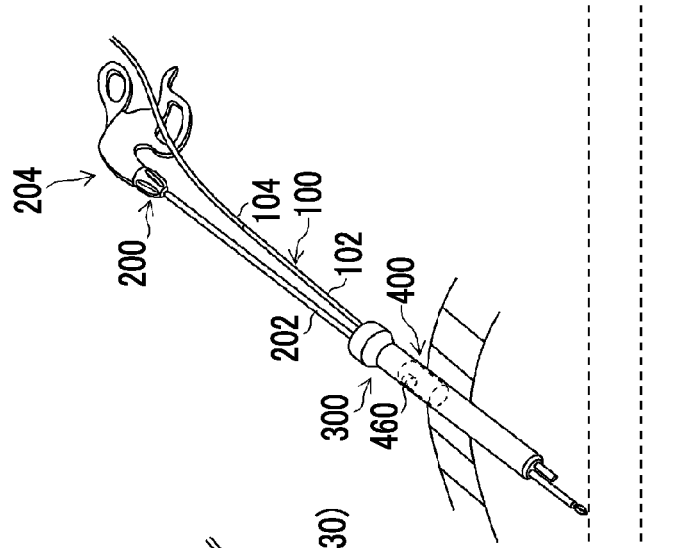
FIG. 29A  FIG. 29B  FIG. 29C
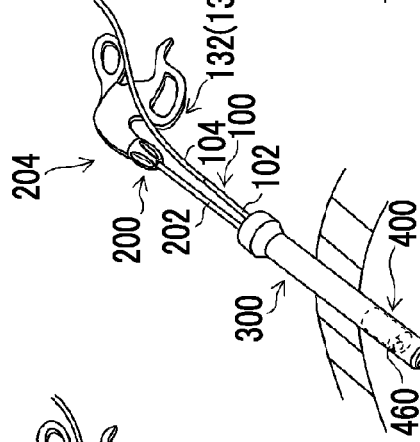
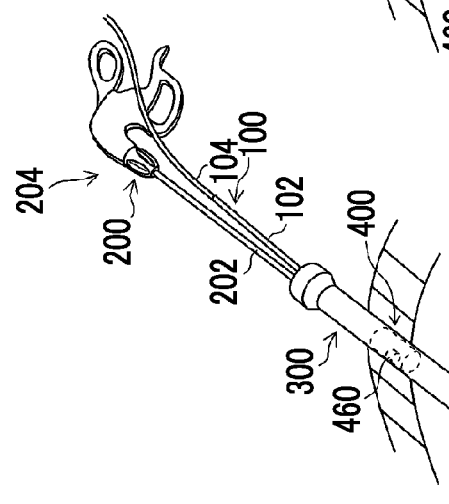

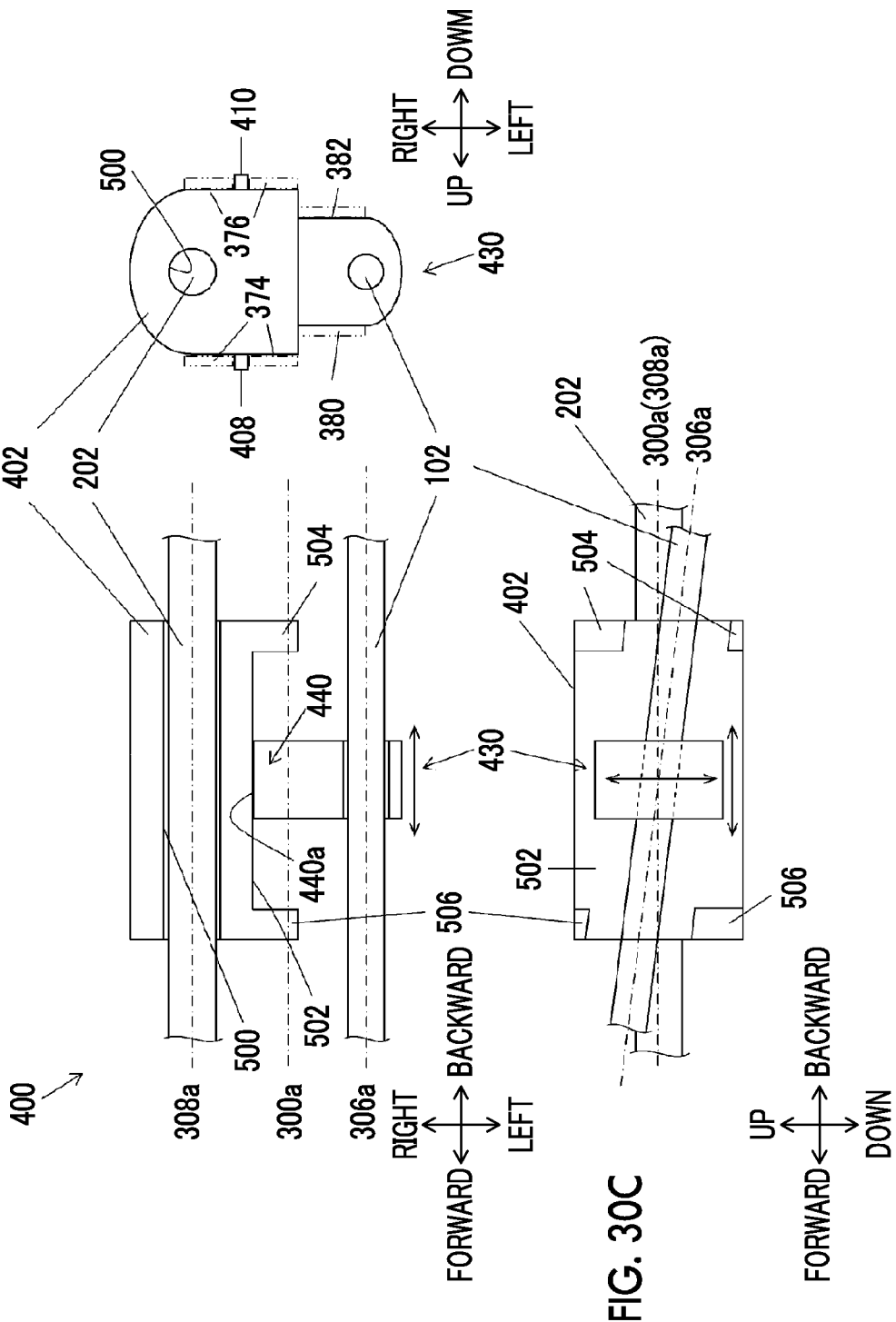

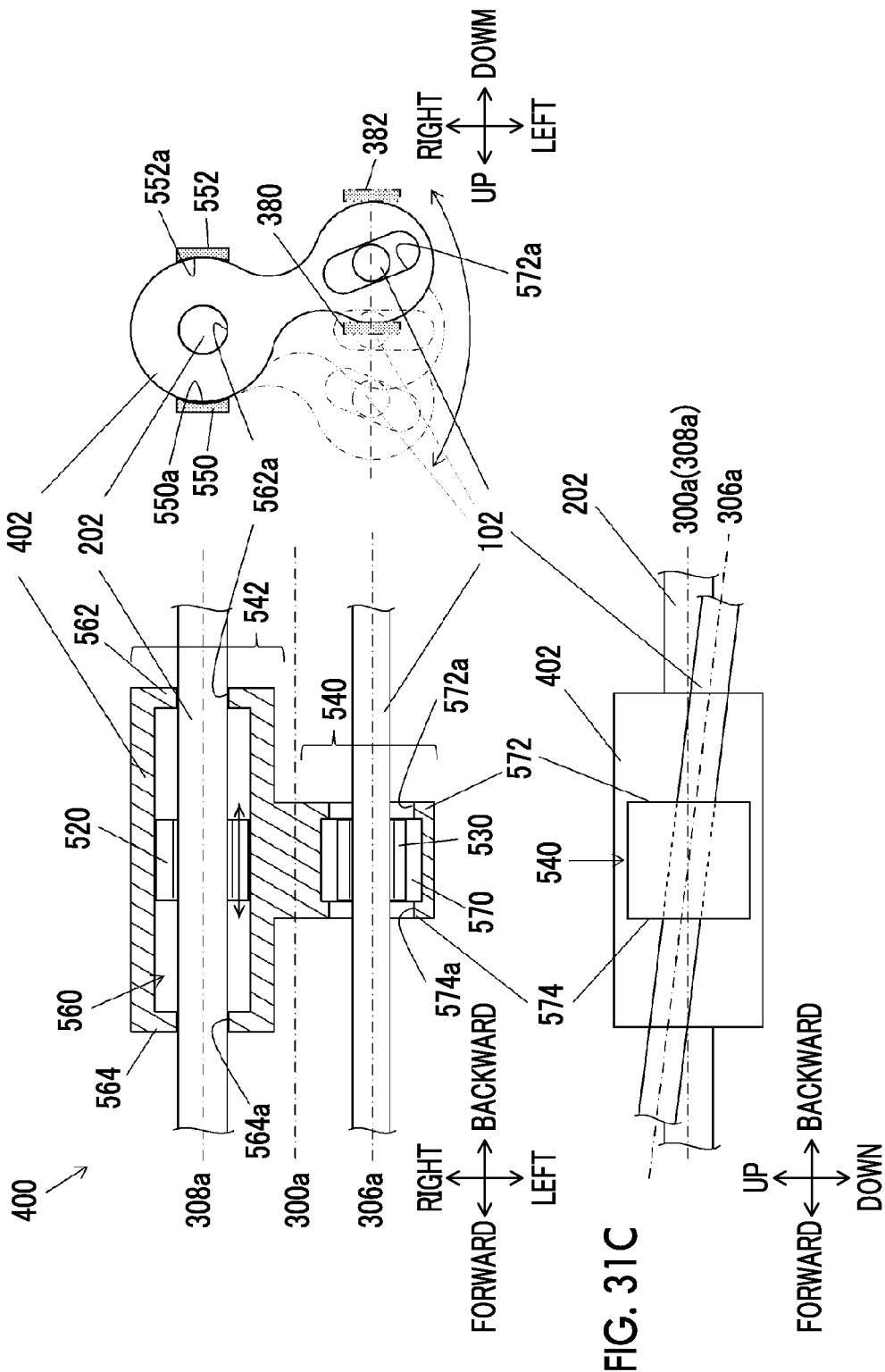

ENDOSCOPIC SURGICAL DEVICE AND OVERTUBE

CROSS-REFERENCE TO RELATED APPLICATIONS

This application is a Continuation of PCT International Application No. PCT/JP2015/059351 filed on Mar. 26, 2015, which claims priority under 35 U.S.C. § 119(a) to U.S. Provisional Application No. 61/971,220 filed on Mar. 27, 2014. Each of the above applications is hereby expressly incorporated by reference, in their entirety, into the present application.

BACKGROUND OF THE INVENTION

1. Field of the Invention

The present invention relates to an endoscopic surgical device and an overtube, and particularly, relates to an endoscopic surgical device and an overtube that can operate an endoscope and a treatment tool inserted through two insertion passages provided in the overtube in an interlocking manner.

2. Description of the Related Art

In recent years, since invasion to a patient is small compared to surgery in which a laparotomy, a thoracotomy, or the like, is performed, endoscopic surgery using endoscopes (hard endoscopes), such as a laparoscope, has been widely performed. In endoscopic surgery, a plurality of holes are made in a patient's body wall, an endoscope is inserted into a body cavity from one hole of these, and a treatment tool is inserted into the body cavity from another hole. Then, treatment of a living body tissue is performed with the treatment tool while observing the living body tissue within the body cavity with the endoscope.

Generally, in endoscopic surgery, one or a plurality of treatment tools are used simultaneously with the endoscope. Therefore, since it is difficult for one surgeon to simultaneously operate the endoscope and the plurality of treatment tools, for example, a task, such as operating a treatment tool that the surgeon holds with his/her hands while making an assistant called an endoscopic technician operate the endoscope is normally performed.

In this way, in endoscopic surgery, it is usual that the surgeon's hands are occupied by the operation of the treatment tool, and the operation of the endoscope is performed by the assistant. Therefore, in a case where the observation position of the endoscope is changed, the surgeon needs to give sequential instructions to the assistant. Hence, the task of correctly directing the orientation of the endoscope to a direction desired by the surgeon is difficult, and stress is likely to be imposed on the surgeon. Additionally, since the assistant performs an operation after the surgeon issues an instruction, there is a tendency that surgery time is likely to be prolonged. Additionally, the assistant needs to operate the endoscope so as not to interfere with a surgeon's procedure, and the operation is likely to become complicated.

In contrast, the present applicant suggests the following technique. In this technique, an overtube that guides an insertion part of an endoscope and an insertion part of a treatment tool into a body cavity includes a tubular overtube body that is inserted in a state where the insertion part of the endoscope and the insertion part of the treatment tool are made to be parallel to each other, a movable body that is movable in an axial direction and has an endoscope holding part and a treatment tool holding part is provided inside the overtube body, the insertion part of the endoscope and the insertion part of the treatment tool are held by the respective holding parts in a state where the insertion parts are made to be parallel to each other, and if the insertion part of the treatment tool is moved in the axial direction, the insertion part of the endoscope also moves in the axial direction in an interlocking manner with this movement (refer to WO2013/176167A). According to this technique, the number of holes made in the patient's body wall can be reduced, the invasion to a patient can be reduced, and the visual field of the endoscope can be easily changed while the surgeon operates the treatment tool without asking for an assistant's help.

Meanwhile, in an overtube (trocar) disclosed in JP2011-520492A, in order to obtain a side surface image of a surgery region and the depth of the visual field, a treatment tool is inserted in an axis direction of an overtube body (main tube member), and an endoscope is inserted in an oblique direction with respect to the axis direction of the overtube body.

Additionally, in an overtube (trocar sleeve) disclosed in JP2011-224376A, a shaft-shaped central portion of an endoscope with a high rigidity, and a shaft portion of a treatment tool are inserted in the state where these portions are made to be parallel to each other. However, in order to prevent interference between the endoscope and the treatment tool inside and outside a body cavity, an operating portion connected to a proximal side of the shaft-shaped central portion of the endoscope and a distal end portion connected to a distal side (body cavity side) are arranged so as to be offset or inclined with respect to a longitudinal axis of the shaft-shaped central portion.

SUMMARY OF THE INVENTION

Meanwhile, in the techniques that the present applicant has previously suggested, it is desirable to bring the two insertion passages provided in the overtube as close to each other as possible to make the external diameter of the overtube small, from a viewpoint of low invasion to a patient. However, if these insertion passages are brought excessively close to each other in order to achieve a decrease in the diameter of the overtube, a visual field direction of the endoscope and a forward-backward movement direction of the treatment tool coincide with each other. Therefore, when the treatment tool approaches a living body tissue within a body cavity, dead areas may be generated by any portions other than the distal end of the treatment tool, and the state of the distal end of the treatment tool may be unable to be checked.

In contrast, the related-art techniques disclosed in the above-described Patent Documents 2 and 3 do not have a configuration in which the endoscope is made to be movable forward and backward in an interlocking manner with the forward and backward movement of the treatment tool, do not take the problem as above into consideration at all, and have no description that suggests means for solving the problem.

The invention has been made in view of such circumstances, and an object thereof is to provide an endoscopic surgical device and an overtube that allow easy checking of the state of a distal end of a treatment tool while achieving a decrease in the diameter of the overtube, and improvement in surgical efficiency, in a configuration in which an endoscope is made to be movable forward and backward in an interlocking manner with the forward and backward movement of a treatment tool.

In order to achieve the above object, the endoscopic surgical device related to an aspect of the invention is an endoscopic surgical device including an endoscope including an endoscope insertion part having an observation part provided at a distal end thereof; a treatment tool including a treatment tool insertion part having a treatment part provided at a distal end thereof; and an overtube that guides the endoscope insertion part and the treatment tool insertion part into a body cavity. The overtube includes an overtube body that passes through a body wall and is inserted into the body cavity, an endoscope insertion passage that is provided inside the overtube body and allows the endoscope insertion part to be inserted therethrough so as to be movable forward and backward, a treatment tool insertion passage that is provided inside the overtube body and allows the treatment tool insertion part to be inserted therethrough so as to be movable forward and backward, and an interlocking member that includes an endoscope engagement part engaged with the endoscope insertion part inserted through the endoscope insertion passage, and a treatment tool engagement part engaged with the treatment tool insertion part inserted through the treatment tool insertion passage and that is arranged inside the overtube body so as to be movable forward and backward. An axial direction of the endoscope insertion passage is an oblique direction with respect to an axial direction of the treatment tool insertion passage, and is provided in a direction in which a distal end of the endoscope insertion part is relatively away from a distal end of the treatment tool insertion part inserted through the treatment tool insertion passage when the endoscope insertion part inserted through the endoscope insertion passage has been moved toward its own distal end side.

According to this aspect, a visual field direction of the endoscope becomes the oblique direction with respect to a forward-backward movement direction of the treatment tool. Thus, when the treatment tool approaches a living body tissue within the body cavity, dead areas are not easily generated by portions other than the distal end of the treatment tool. Therefore, the state of the distal end of the treatment tool can easily be checked while achieving a decrease in the diameter of the overtube, and it is possible to improve surgical efficiency, in a configuration in which the endoscope is made to be movable forward and backward in an interlocking manner with the forward and backward movement of the treatment tool.

In the endoscopic surgical device related to the aspect of the invention, an aspect in which the axial direction of the endoscope insertion passage is provided obliquely to the axial direction of the overtube body is preferable.

In the endoscopic surgical device related to the aspect of the invention, an aspect in which the axial direction of the treatment tool insertion passage is provided parallel to the axial direction of the overtube body is preferable.

In the endoscopic surgical device related to the aspect of the invention, an aspect in which the interlocking member includes an adjusting mechanism that adjusts the distance between the endoscope engagement part and the treatment tool engagement part according to the position of the interlocking member in the axial direction of the overtube body is preferable.

As a form of the above aspect, there is an aspect in which the adjusting mechanism causes any one of the endoscope engagement part and the treatment tool engagement part to slide in a direction having a movement component perpendicular to the axial direction of the overtube body with respect to the other engagement part, along with the forward and backward movement of the endoscope insertion part or the treatment tool insertion part.

For example, the adjusting mechanism may include a guide projection that is provided in any one of the endoscope engagement part and the treatment tool engagement part, and a guide groove that is provided in the other of the endoscope engagement part and the treatment tool engagement part and causes the guide projection to slide in a direction having a movement component perpendicular to the axial direction of the overtube body.

Additionally, as a form of the above aspect, there is an aspect in which the adjusting mechanism includes the interlocking member that is provided so as to be rotatable with respect to the longitudinal axis of the overtube body, an endoscope-side insertion hole that is provided in the interlocking member and rotatably holds the endoscope engagement part, and a treatment-tool-side insertion hole that is provided in the interlocking member, and rotatably holds the treatment tool engagement part, and any one insertion hole of the endoscope-side insertion hole and the treatment-tool-side insertion hole includes an elongated hole that extends in a direction perpendicular to the longitudinal axis of the endoscope insertion part or the treatment tool insertion part inserted through the other insertion hole.

In the endoscopic surgical device related to the aspect of the invention, an aspect in which the interlocking member includes a dead zone where the forward and backward movement of either the endoscope insertion part or the treatment tool insertion part does not interlock with the movement of the other and a sensing zone where the forward and backward movement of either the endoscope insertion part or the treatment tool insertion part interlocks with the movement of the other is preferable.

The overtube related to another aspect of the invention is an overtube that guides an endoscope including an endoscope insertion part having an observation part provided at a distal end thereof, and a treatment tool including a treatment tool insertion part having a treatment part provided at a distal end thereof into a body cavity. The overtube includes an overtube body that passes through a body wall and is inserted into the body cavity; an endoscope insertion passage that is provided inside the overtube body and allows the endoscope insertion part to be inserted therethrough so as to be movable forward and backward; a treatment tool insertion passage that is provided inside the overtube body and allows the treatment tool insertion part to be inserted therethrough so as to be movable forward and backward, and an interlocking member that includes an endoscope engagement part engaged with the endoscope insertion part inserted through the endoscope insertion passage, and a treatment tool engagement part engaged with the treatment tool insertion part inserted through the treatment tool insertion passage and that is arranged inside the overtube body so as to be movable forward and backward. An axial direction of the endoscope insertion passage is an oblique direction with respect to an axial direction of the treatment tool insertion passage, and is provided in a direction in which the endoscope insertion part and the treatment tool insertion part are provided in directions away from each other at a distal end side.

According to the invention, the state of the distal end of the treatment tool can easily be checked while achieving a decrease in the diameter of the overtube, and it is possible to improve surgical efficiency, in a configuration in which the endoscope is made to be movable forward and backward in an interlocking manner with the forward and backward movement of the treatment tool.

BRIEF DESCRIPTION OF THE DRAWINGS

FIG. 26 is an explanatory view used for the description of the action of the slider and is a sectional view of the slider cut at the same position as that of FIG. 14.

FIG. 27 is an explanatory view used for the description of the action of the slider and is a sectional view of the slider cut at the same position as that of FIG. 14.

FIGS. 28A to 28C are views illustrating an aspect of the forward and backward movement operation in a dead zone.

FIGS. 29A to 29C are views illustrating an aspect of the forward and backward movement operation in a sensing zone.

FIGS. 30A to 30C are schematic views illustrating a second embodiment of the slider.

FIGS. 31A to 31C are schematic views illustrating a third embodiment of the slider.

DESCRIPTION OF THE PREFERRED EMBODIMENTS

Preferred embodiments of the invention will be described below in detail according to the accompanying drawings. In addition, any of the drawings may illustrate main parts in an exaggerated manner for description, and may have dimensions different from actual dimensions.

Figure 1:
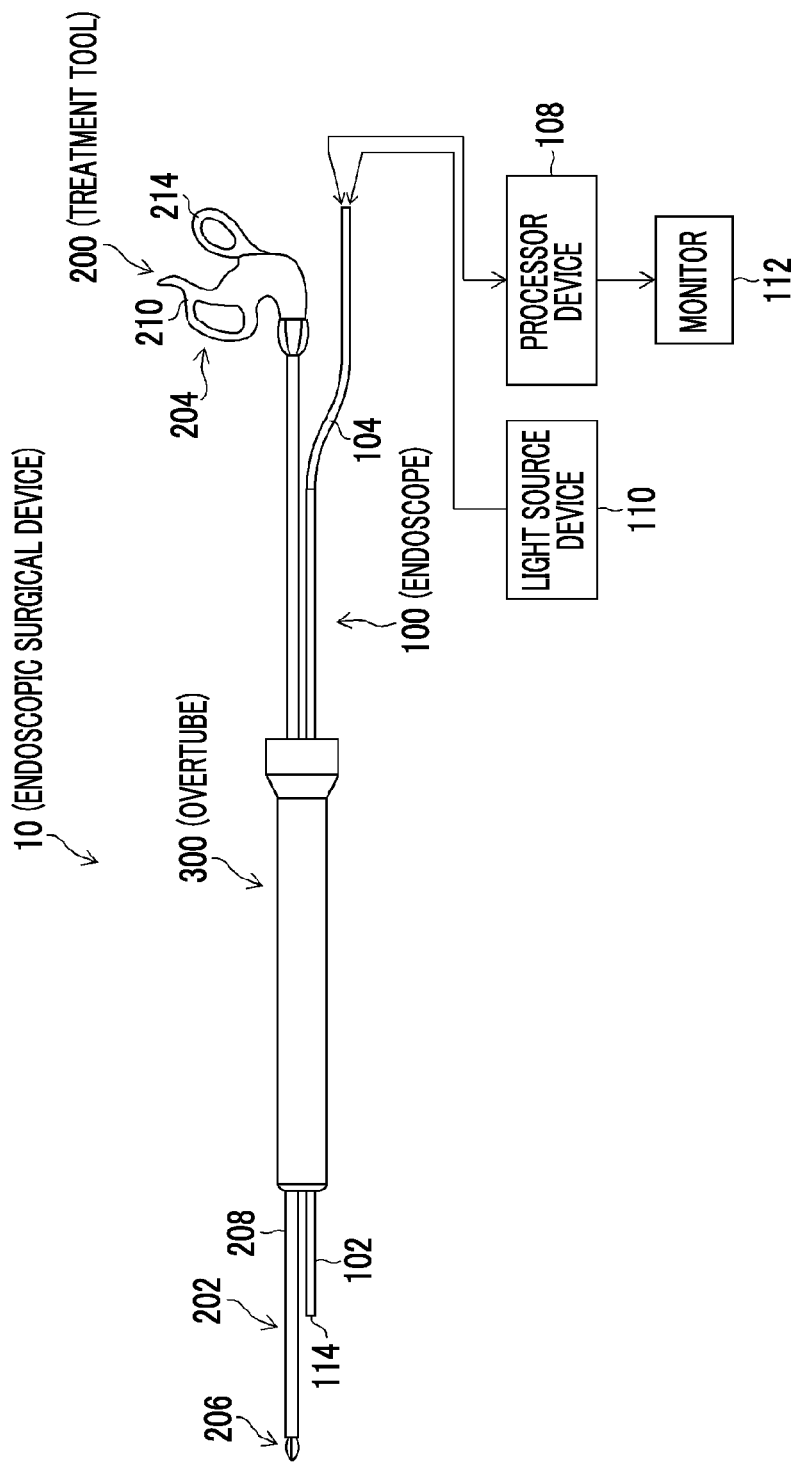
FIG. 1 is a schematic block diagram of an endoscopic surgical device related to the invention.

FIG. 1 is a schematic block diagram of an endoscopic surgical device related to the invention. As illustrated in FIG. 1, an endoscopic surgical device 10 includes an endoscope 100 that observes the inside of a patient's body cavity, a treatment tool 200 for examining or treating a diseased site within the patient's body cavity, and an overtube 300 that guides the endoscope 100 and the treatment tool 200 into the body cavity.

As illustrated in FIG. 1, the endoscope 100 is, for example, a hard endoscope, such as a laparoscope, and includes an insertion part (hereinafter referred to as "endoscope insertion part") 102 that is inserted into a body cavity and has an outer peripheral part surrounded by an elongated hard tubular body, and a cable part 104 that is provided continuously with a base end side of the endoscope insertion part 102 and that has an outer peripheral part surrounded by an elongated flexible tubular body.

The cable part 104 indicates a flexible cable portion in which a wire rod, such as a cable or a light guide, which extends from a base end of the endoscope insertion part 102, is housed by covering the wire rod with, for example, a flexible insulating member, such as polyvinyl chloride.

A connector (not illustrated) is provided at an end of the cable part 104 on its extension destination, and each of a processor device 108 and a light source device 110 is detachably connected to the cable part via the connector. Additionally, the processor device 108 is connected to a monitor 112 via a cable.

Figure 2:
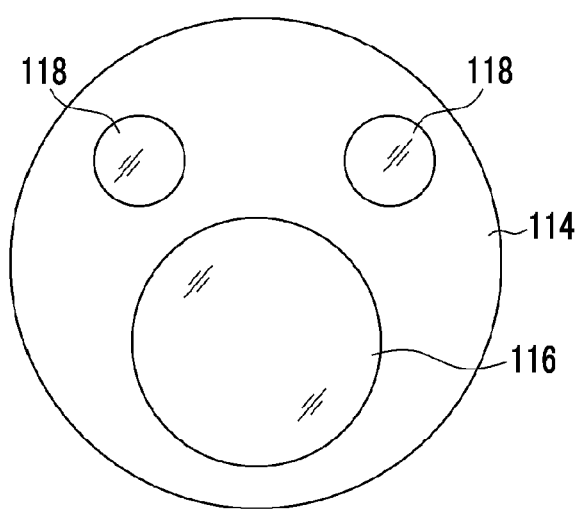
FIG. 2 is a plan view illustrating a distal end surface of an endoscope insertion part.

As illustrated in FIG. 2, a distal end surface 114 of the endoscope insertion part 102 is provided with an observation window 116 and illumination windows 118 and 118.

The observation window 116 is a constituent element of an observation part of the endoscope 100, and an objective lens of an observation optical system, and an image pick-up element, such as a charge coupled device (CCD) or a complementary metal oxide semiconductor (CMOS), which is arranged at an image pick-up position of the objective lens, are disposed behind the observation window 116. A signal cable (not illustrated) is connected to a substrate that supports the image pick-up element. The signal cable is inserted through the endoscope insertion part 102 and the cable part 104 of FIG. 1, is provided to extend up to the connector (not illustrated), and is connected to the processor device 108. An observation image picked up from the observation window 116 is formed on a light-receiving surface of the image pick-up element, and is converted into electrical signals (image pick-up signals), and the electrical signals are output to the processor device 108 via the signal cable and are converted into video signals. Then, the video signals are output to the monitor 112 connected to the processor device 108, and the observation image (endoscope image) is displayed on a screen of the monitor 112.

An exit end of the light guide (not illustrated) is disposed behind the illumination windows 118 and 118 of FIG. 2. The light guide is inserted through the endoscope insertion part 102 and the cable part 104 of FIG. 1 and has an incident end disposed within the connector (not illustrated). Therefore, by coupling the connector to the light source device 110, the illumination light radiated from the light source device 110 is transmitted to the illumination windows 118 and 118 via the light guide, and is radiated forward from the illumination windows 118 and 118. In addition, in FIG. 2, the two illumination windows 118 and 118 are disposed on the distal end surface 114 of the endoscope insertion part 102. However, the number of illumination windows 118 is not limited, and the number thereof may be one or may be three or more. Additionally, the endoscope 100 may not include the light guide.

As illustrated in FIG. 1, the treatment tool 200 consists of, for example, forceps, and includes an elongated insertion part (hereinafter referred to as a "treatment tool insertion part") 202 that is inserted into a body cavity, an operating part 204 that is provided on the base end side of the treatment tool insertion part 202 and is gripped by a surgeon, and a treatment part 206 that is provided on a distal end side of the treatment tool insertion part 202 and is operable by the operation of the operating part 204.

The treatment tool insertion part 202 is provided with a tubular sheath 208, and an operating shaft (not illustrated) that is inserted into the sheath 208 so as to be movable in the direction of an axial center. Moreover, the operating part 204 is provided with a fixed handle 210, and a movable handle 214 that is turnably coupled to the fixed handle 210 via a turning pin. A base end of the operating shaft is coupled to the movable handle 214.

The treatment part 206 is provided with a pair of gripping members that is openable and closable. The gripping members are coupled to a distal end of the operating shaft via a driving mechanism (not illustrated). With the turning operation of the movable handle 214 of the operating part 204, the gripping members of the treatment part 206 are opened and closed via the operating shaft and the driving mechanism.

In addition, the treatment tool 200 is not limited to the forceps, and may be, for example, other treatment tools, such as a laser probe, a suture device, an electric scalpel, a needle holder, and an ultrasonic aspirator.

As illustrated in FIG. 1, the overtube 300 allows the endoscope insertion part 102 and the treatment tool insertion part 202, which are inserted thereinto from the base end side, to be inserted therethrough and delivered from the distal end side. By inserting the overtube 300 into a body wall and having a distal end side thereof arranged outside of the body and a base end side thereof arranged within the body cavity, it is possible to guide the endoscope insertion part 102 and the treatment tool insertion part 202 into the body cavity by one overtube 300. Additionally, the overtube 300 includes an interlocking function of interlocking the endoscope insertion part 102 with the treatment tool insertion part 202 to move these insertion parts forward and backward as will be described below in detail. For example, the endoscope insertion part 102 can also be moved forward and backward by the forward and backward movement operation of only the treatment tool insertion part 202, and a suitable observation image can be obtained without performing the forward and backward movement operation of the endoscope insertion part 102.

Figure 3:
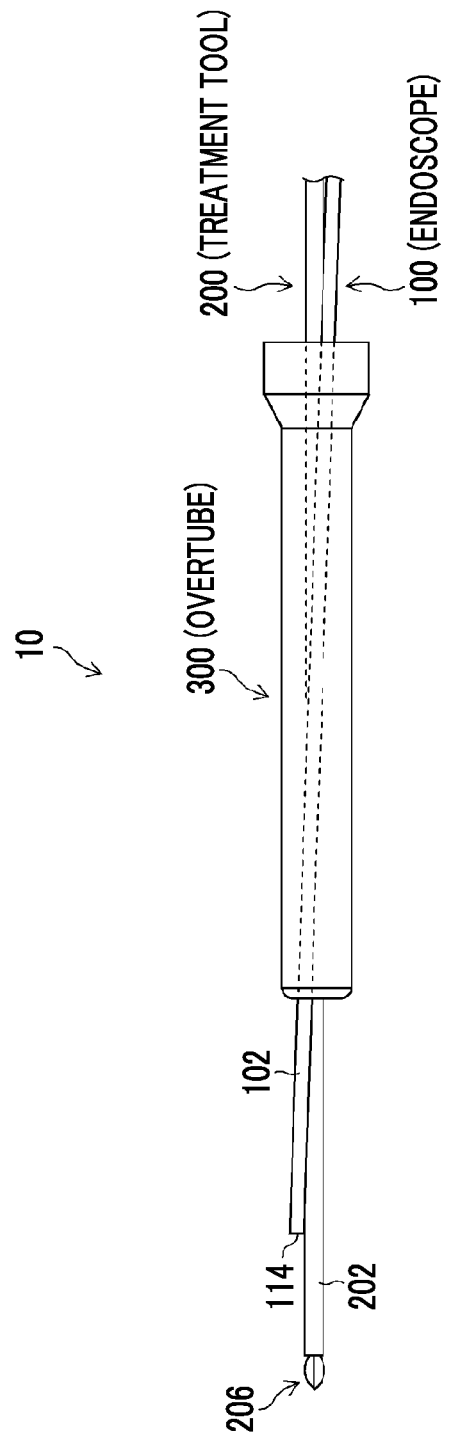
FIG. 3 is a view illustrating an overtube, an endoscope, and a treatment tool from the lower side in FIG. 1.

Moreover, the overtube 300 guides the endoscope insertion part 102 in an oblique direction with respect to a guide direction of the treatment tool insertion part 202 as illustrated in FIG. 3 illustrating the overtube 300 from the lower side in FIG. 1. Accordingly, a distal end of the treatment part 206 can be visually recognized on an observation image by widening the spacing between the observation part (observation window 116) at a distal end of the endoscope insertion part 102 and the treatment part 206 at a distal end of the treatment tool insertion part 202 so that a distal end portion of the treatment part 206 at the distal end of the treatment tool insertion part 202 does not become a dead area.

Figure 4:
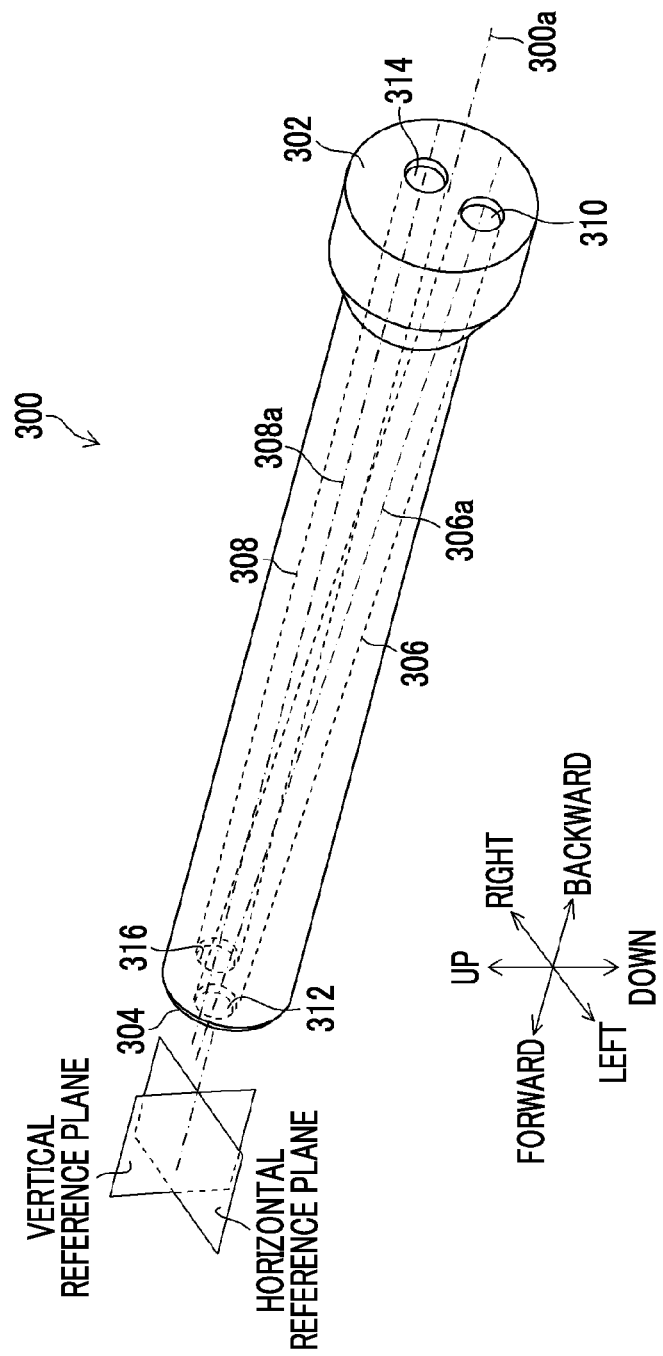
FIG. 4 is an external perspective view illustrating the overtube.

FIG. 4 is an external perspective view illustrating the overtube 300.

Here, as illustrated in this drawing, with respect to the position and direction in a space where the overtube 300 is arranged, a direction along a reference axis 300a (longitudinal axis) that becomes a central axis of the entire overtube 300 is defined as a forward-backward direction. In a case where a plane in a predetermined direction including the reference axis 300a is defined as a horizontal reference plane, and a plane including the reference axis 300a and being orthogonal to the horizontal reference plane is defined as a vertical reference plane, a direction orthogonal to the horizontal reference plane is defined as an upward-downward direction, and a direction orthogonal to vertical reference plane is defined as a leftward-rightward direction.

As illustrated in this drawing, the overtube 300 has an endoscope insertion passage 306 through which the endoscope insertion part 102 of the endoscope 100 is inserted so as to be movable forward and backward, and a treatment tool insertion passage 308 through which the treatment tool insertion part 202 of the treatment tool 200 is inserted so as to be movable forward and backward.

The endoscope insertion passage 306 is provided on a left side with respect to the reference axis 300a (vertical reference plane), has at least a diameter such that the endoscope insertion part 102 can be inserted therethrough with an endoscope insertion axis 306a as a central axis, and passes through the inside of the overtube 300 from a base end surface 302 of the overtube 300 to a distal end surface 304 thereof. The endoscope insertion axis 306a is equivalent to the position of an axis (central axis) of the endoscope insertion part 102 that is inserted through the endoscope insertion passage 306.

Additionally, the endoscope insertion axis 306a is made oblique to the direction of the reference axis 300a. Thus, in a case where the reference axis 300a and the endoscope insertion axis 306a are projected on the horizontal reference plane, these axes are parallel to each other on the horizontal reference plane, but these axes are not parallel to each other on the vertical reference plane in a case where these axes are projected on the vertical reference plane, and the endoscope insertion axis 306a is inclined obliquely from a rear lower side toward a front upper side. Additionally, it is desirable that the endoscope insertion axis 306a intersects the horizontal reference plane at least within a range of the overtube 300. In the present embodiment, for example, the endoscope insertion axis 306a intersects the horizontal reference plane at a substantially intermediate position in the direction of reference axis 300a of the overtube 300.

The base end surface 302 is provided with an endoscope insertion port 310 that allows the endoscope insertion part 102 to be inserted into the endoscope insertion passage 306 therethrough, and the distal end surface 304 is provided with an endoscope delivery port 312 that allows the endoscope insertion part 102 inserted into the endoscope insertion passage 306 to be delivered to the outside therethrough.

Although both of the center of the endoscope insertion port 310 and the center of the endoscope delivery port 312 are located on the endoscope insertion axis 306a, the center of the endoscope insertion port 310 is located below the horizontal reference plane, and the center of the endoscope delivery port 312 is located above the horizontal reference plane.

The treatment tool insertion passage 308 is located on a right side with respect to the reference axis 300a (vertical reference plane), has at least a diameter such that the treatment tool insertion part 202 can be inserted therethrough with a treatment tool insertion axis 308a as a central axis, and passes through the inside of the overtube 300 from the base end surface 302 of the overtube 300 to the distal end surface 304 thereof. The treatment tool insertion axis 308a is equivalent to the position of an axis (central axis) of the treatment tool insertion part 202 that is inserted through the treatment tool insertion passage 308.

Additionally, the treatment tool insertion axis 308a is parallel to the direction of the reference axis 300a. Thus, the treatment tool insertion axis 308a is parallel to the reference axis 300a on both of the horizontal reference plane and the vertical reference plane in a case where the reference axis 300a and the treatment tool insertion axis 308a are projected on each of the vertical reference plane and the horizontal reference plane. Additionally, the treatment tool insertion axis 308a is on the horizontal reference plane, and has a left and right positional relationship with the reference axis 300a.

The base end surface 302 is provided with a treatment tool insertion port 314 for allowing the treatment tool insertion part 202 to be inserted into the treatment tool insertion passage 308 therethrough, and the distal end surface 304 is provided with a treatment tool delivery port 316 for allowing the treatment tool insertion part 202 inserted into the treatment tool insertion passage 308 to be delivered to the outside therethrough.

Both of the center of the treatment tool insertion port 314 and the center of the treatment tool delivery port 316 are located on the treatment tool insertion axis 308a, and are located on the horizontal reference plane.

According to the arrangement of the endoscope insertion passage 306 and the treatment tool insertion passage 308 in the overtube 300 as above, the direction of the endoscope insertion axis 306a is an oblique direction with respect to the direction of the treatment tool insertion axis 308a. Thus, when the endoscope insertion part 102 inserted through the endoscope insertion passage 306 is moved toward the distal end side, the distal end of the endoscope insertion part 102 is provided in a direction relatively away from the distal end of the treatment tool insertion part 202 inserted through the treatment tool insertion passage 308. That is, the position of the distal end (distal end surface 114) of the endoscope insertion part 102 that inserted through the endoscope insertion passage 306 and delivered from the endoscope delivery port 312 has a greater separation distance in a radial direction with respect to the treatment tool insertion part 202 (treatment tool insertion axis 308a) inserted through the treatment tool insertion passage 308, as the amount of protrusion from the endoscope delivery port 312 becomes greater.

Figure 5:
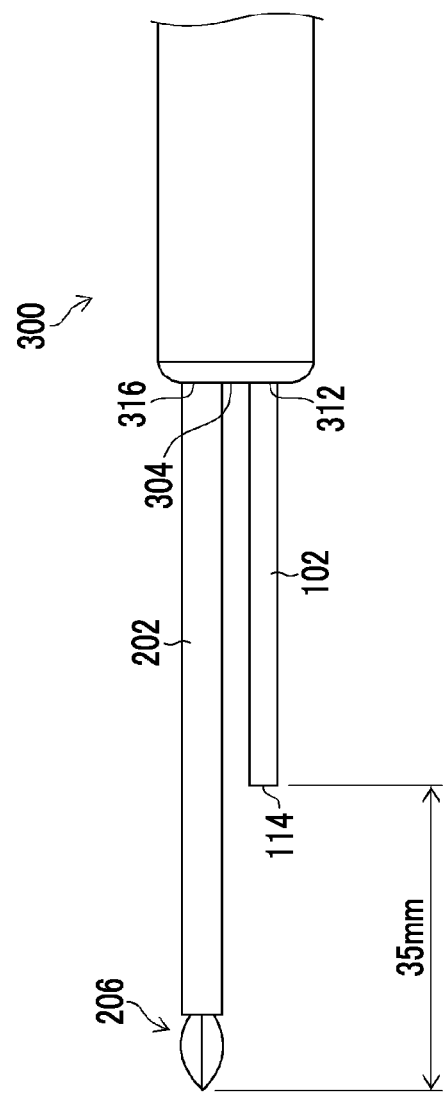
FIG. 5 is a view illustrating an aspect of the endoscope insertion part and a treatment tool insertion part on a distal end side inserted in parallel through the overtube.

Here, in a case where the endoscope insertion passage 306 (endoscope insertion axis 306a) in the overtube 300 is provided parallel to the treatment tool insertion passage 308 (treatment tool insertion axis 308a), the endoscope insertion part 102 and the treatment tool insertion part 202, respectively, delivered from the endoscope delivery port 312 and the treatment tool delivery port 316 in the distal end surface 304 of the overtube 300 approach each other, as illustrated in FIG. 5, with a decrease in the diameter of the overtube 300.

Figure 6:
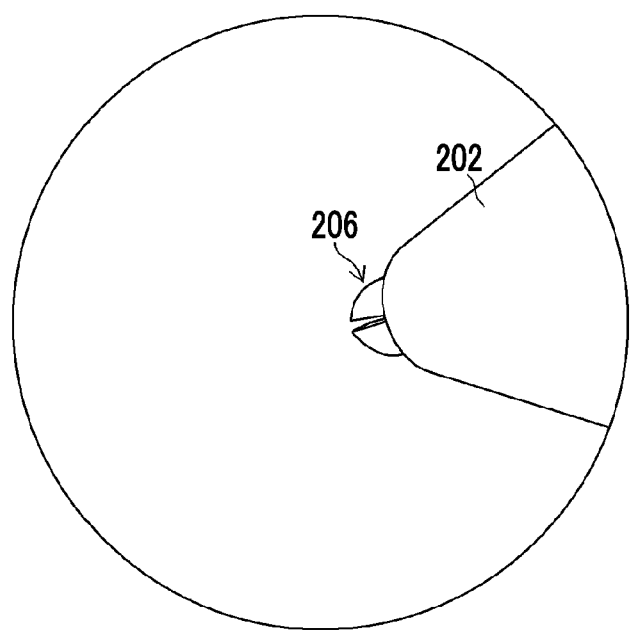
FIG. 6 is a view illustrating an observation image obtained in the state of FIG. 5.

Therefore, even if the amount of protrusion of the treatment tool insertion part 202 from the treatment tool delivery port 316 and the amount of protrusion of the endoscope insertion part 102 from the endoscope delivery port 312 are adjusted (for example, a state where the amount of protrusion of the treatment tool insertion part 202 is 35 mm greater than the amount of protrusion of the endoscope insertion part 102) so that the treatment part 206 at the distal end of the treatment tool insertion part 202 is reflected within a visual field range of the observation part provided at the distal end of the endoscope insertion part 102, there is a concern that dead areas may be generated by portions other than the distal end of the treatment part 206, and a situation where the state of the distal end of the treatment part 206 cannot be checked may occur, as in an observation image illustrated in FIG. 6.

Figure 7:
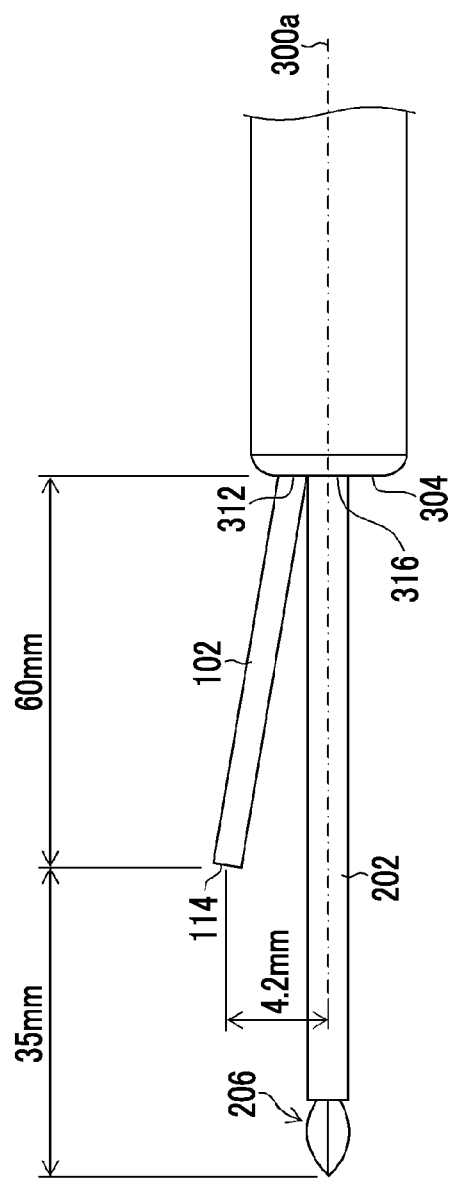
FIG. 7 is a view illustrating an aspect of the endoscope insertion part and the treatment tool insertion part on the distal end side inserted through the overtube of the present embodiment.

Meanwhile, in a case where the endoscope insertion passage 306 (endoscope insertion axis 306a) and the treatment tool insertion passage 308 (treatment tool insertion axis 308a) are obliquely provided as in the overtube 300 of the present embodiment, the endoscope insertion part 102 and the treatment tool insertion part 202, respectively, delivered from the endoscope delivery port 312 and the treatment tool delivery port 316 in the distal end surface 304 of the overtube 300 can be separated from each other as illustrated in FIG. 7.

Figure 8:
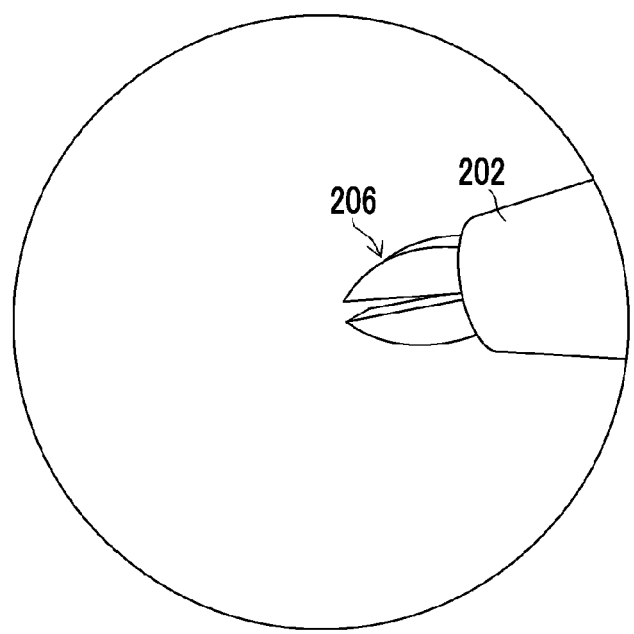
FIG. 8 is a view illustrating an observation image obtained in the state of FIG. 7.

Accordingly, the spacing between the observation part at the distal end of the endoscope insertion part 102 and the treatment part 206 at the distal end of the treatment tool insertion part 202 can be increased, and even in a case where the diameter of the overtube 300 is reduced, dead areas are not easily generated by portions other than the distal end of the treatment part 206, and a portion up to the distal end of the treatment part 206 of the treatment tool insertion part 202 can be visually recognized, as in an observation image illustrated in FIG. 8.

For example, in the standard usage under treatment, the amount of protrusion (the amount of protrusion from the treatment tool delivery port 316 or the distal end surface 304) of the treatment tool insertion part 202 is set to 60 mm, and the amount of protrusion (the amount of protrusion from the endoscope delivery port 312 or the distal end surface 304) of the endoscope insertion part 102 is set to 95 mm. In this case, in order for the portion up to the distal end of the treatment part 206 to be capable of being observed without any dead area on the observation image, it is preferable to incline the endoscope insertion passage 306 (endoscope insertion axis 306a) with respect to the treatment part insertion axis 308a so that the center of the observation window 116 is separated from the horizontal reference plane by 4.2 mm.

Additionally, it is preferable that the inclination of the endoscope insertion axis 306a with respect to the reference axis 300a (treatment tool insertion axis 308a) when the endoscope insertion axis is projected on the vertical reference plane is 2 degrees. In this case, in order for the center of the observation window 116 be separated from the horizontal reference plane by 4.2 mm, a position where the endoscope insertion axis 306a intersects the horizontal reference plane becomes a position where the length from the endoscope delivery port 312 (or the distal end surface 304 of the overtube 300) to the base end side is (4.2/tan(2°)– 60 (=about 60 mm).

In addition, in a case where the endoscope insertion axis 306a is made oblique to the treatment tool insertion axis 308a as in the present embodiment, the distal end portion of the treatment part 206 is reflected on a peripheral edge on the observation image if a direct viewing type endoscope in which the center of the visual field range is made oblique to an axis direction of the endoscope insertion part 102 is used as the endoscope 100. Although the observation image obtained by the endoscope 100 may be displayed on the monitor 112 as it is, the observation image may be partially cut off and processed so that the distal end portion of the treatment part 206 is located in the vicinity of the center of the observation image, and may be displayed on the monitor 112. In addition, the distal end portion of the treatment part 206 may be reflected in the vicinity of the center of the observation image, using the direct viewing type endoscope in which the center of the visual field range becomes oblique to the axis direction of the endoscope insertion part 102, as the endoscope 100.

Figure 9:
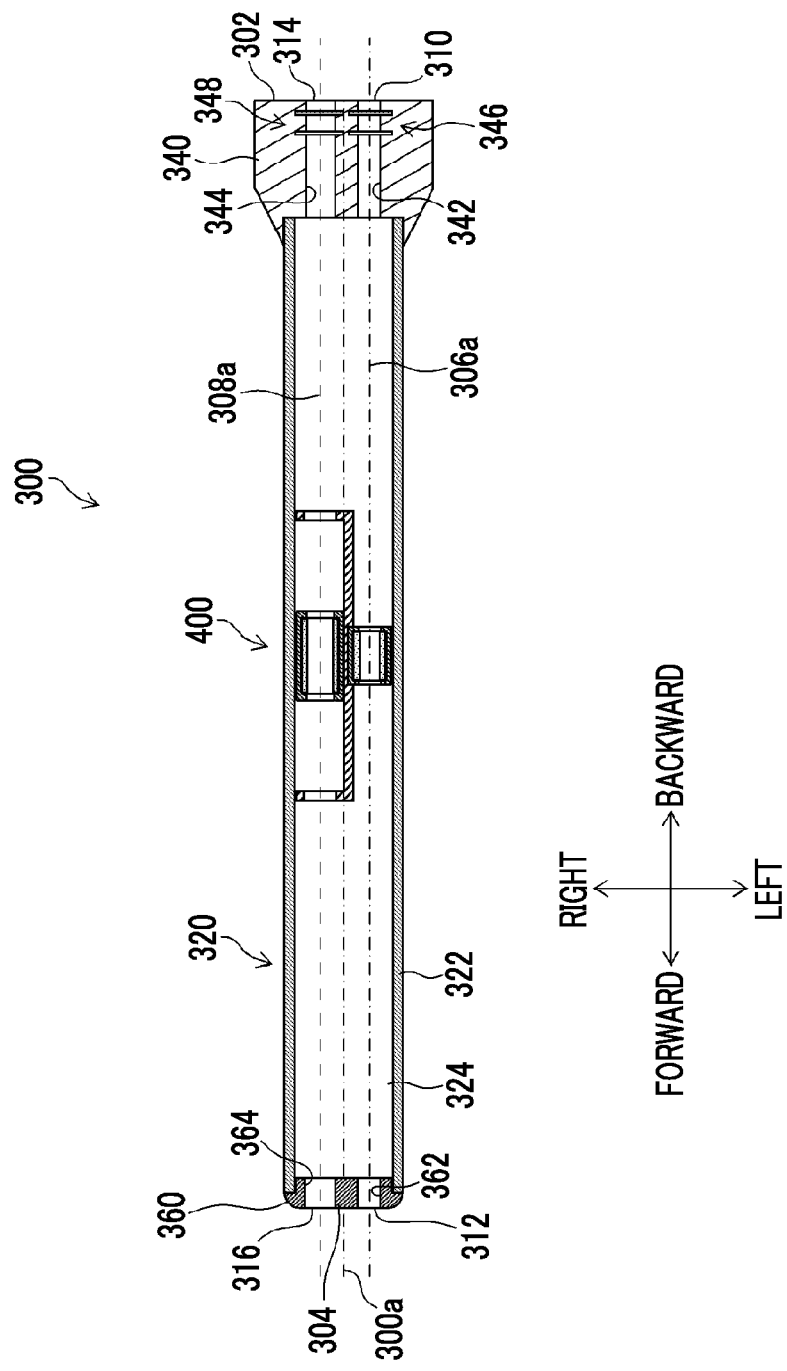
FIG. 9 is a horizontal sectional view illustrating the internal structure of the overtube.

The specific configuration of the overtube 300 will be described. FIG. 9 illustrates a horizontal section cut by thee horizontal reference plane illustrating the internal structure of the overtube 300.

As illustrated in this drawing, the overtube 300 has an overtube body 320 that occupies substantially the entire area, a base end cap 340 that is arranged at a rear part of the overtube 300, a distal end cap 360 that is arranged at a distal end, and a slider 400 (the slider 400 is one form of an interlocking member) that is arranged inside the overtube 300. In addition, the base end cap 340 and the distal end cap 360 are some of the constituent elements of the overtube body of the invention, and may be formed separately from or formed integrally with the overtube body 320.

The overtube body 320 is formed in an elongated cylindrical shape having the reference axis 300*a* as a central axis using hard resins, metals, or the like, and has an outer wall 322 that surrounds an outer periphery, and a cavity part 324 that penetrates from a base end of the overtube body 320 to a distal end thereof.

The cavity part 324 has the endoscope insertion axis 306*a* and the treatment tool insertion axis 308*a* inserted therethrough, and is provided with a space that serves as the endoscope insertion passage 306 and the treatment tool insertion passage 308.

The base end cap 340 is attached to the base end of the overtube body 320, and is formed in a columnar shape made to have a greater diameter than the external diameter of the overtube body 320, using hard resins, metals, or the like. The base end cap 340 has a flat rear end surface serving as the base end surface 302 of the overtube 300 on a rear side thereof, and has through-holes 342 and 344 that penetrate from the base end surface 302 to the cavity part 324 of the overtube body 320.

The through-hole 342 has a central axis arranged coaxially with the endoscope insertion axis 306*a* that becomes oblique to the reference axis 300*a*, and forms a portion of the endoscope insertion passage 306. An opening of the through-hole 342 in the base end surface 302 is equivalent to the above-described endoscope insertion port 310.

The through-hole 344 has a central axis arranged coaxially with the treatment tool insertion axis 308*a* that is parallel to the reference axis 300*a*, and forms a portion of the treatment tool insertion passage 308. An opening of the through-hole 344 in the base end surface 302 is equivalent to the above-described treatment tool insertion port 314.

Valve members 346 and 348 are respectively arranged in the through-hole 342 and the through-hole 344. Although the detailed description of the valve members 346 and 348 is omitted, for example, the valve members have slits that open only in a case where the endoscope insertion part 102 and the treatment tool insertion part 202 are inserted therethrough and that come into close contact with outer peripheral surfaces (side surfaces) of the endoscope insertion part 102 and the treatment tool insertion part 202 without a substantial gap. This secures the airtightness of spaces closer to the distal end side than the valve members 346 and 348, and reduces the leakage or the like of a pneumoperitoneum gas injected into the body cavity to the outside of the body.

In addition, the valve members 346 and 348 are not limited to those with the specific configuration, and valve members with widely-known arbitrary configurations can be used. Although FIG. 9 illustrates a configuration in which the two valve members are respectively arranged in the through-hole 342 and the through-hole 344, a configuration in which one valve member or three or more valve members are arranged may be adopted.

The distal end cap 360 illustrated in FIG. 9 is attached to the distal end of the overtube body 320, and is formed of hard resins, metals, or the like. The distal end cap 360 has a front surface serving as the distal end surface 304 of the overtube 300 on a front side thereof, and has through-holes 362 and 364 that penetrate from the cavity part 324 of the overtube body 320 to the distal end surface 304.

The through-hole 362 has a central axis arranged coaxially with the endoscope insertion axis 306*a* that becomes oblique to the reference axis 300*a*, and forms a portion of the endoscope insertion passage 306. An opening of the through-hole 362 in the distal end surface 304 is equivalent to the above-described endoscope delivery port 312.

The through-hole 364 has a central axis arranged coaxially with the treatment tool insertion axis 308*a* that is parallel to the reference axis 300*a*, and forms a portion of the treatment tool insertion passage 308. An opening of the through-hole 364 in the distal end surface 304 is equivalent to the above-described treatment tool delivery port 316.

Next, the slider 400 will be described.

As illustrated in FIG. 9, the slider 400 is housed within the overtube body 320 (within the cavity part 324), and is supported so as to be movable forward and backward in the direction (forward-backward direction) of the reference axis 300*a*.

Figure 10:
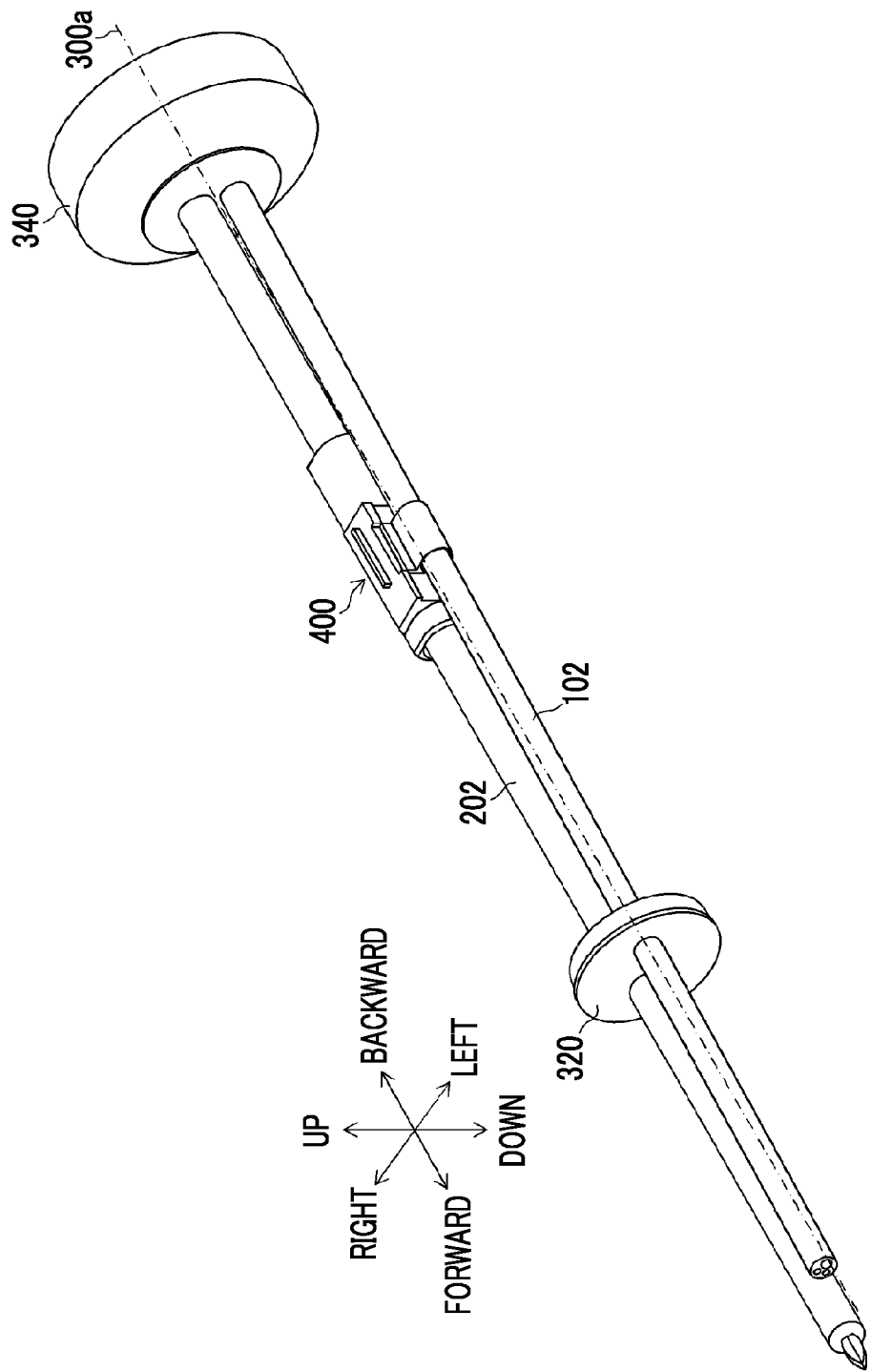
FIG. 10 is a perspective view of the overtube illustrating only a slider within an overtube body.

As illustrated in FIG. 10 illustrating only the slider 400 with the overtube body 320 (outer wall 322) being omitted, the slider 400 functions as an interlocking member that is coupled to the endoscope insertion part 102 inserted through the endoscope insertion passage 306 and the treatment tool insertion part 202 inserted through the treatment tool insertion passage 308 and that has a dead zone where the forward and backward movement of either the endoscope insertion part 102 or the treatment tool insertion part 202 in the forward-backward direction (axial direction) does not interlock with the movement of the other and a sensing zone where the forward and backward movement of either the endoscope insertion part or the treatment tool insertion part interlocks with the movement of the other. That is, the slider 400 interlocks the endoscope insertion part 102 with the treatment tool insertion part 202 with play with respect to the forward and backward movement in the forward-backward direction.

The internal structure of the slider 400 will be described.

Figure 11:
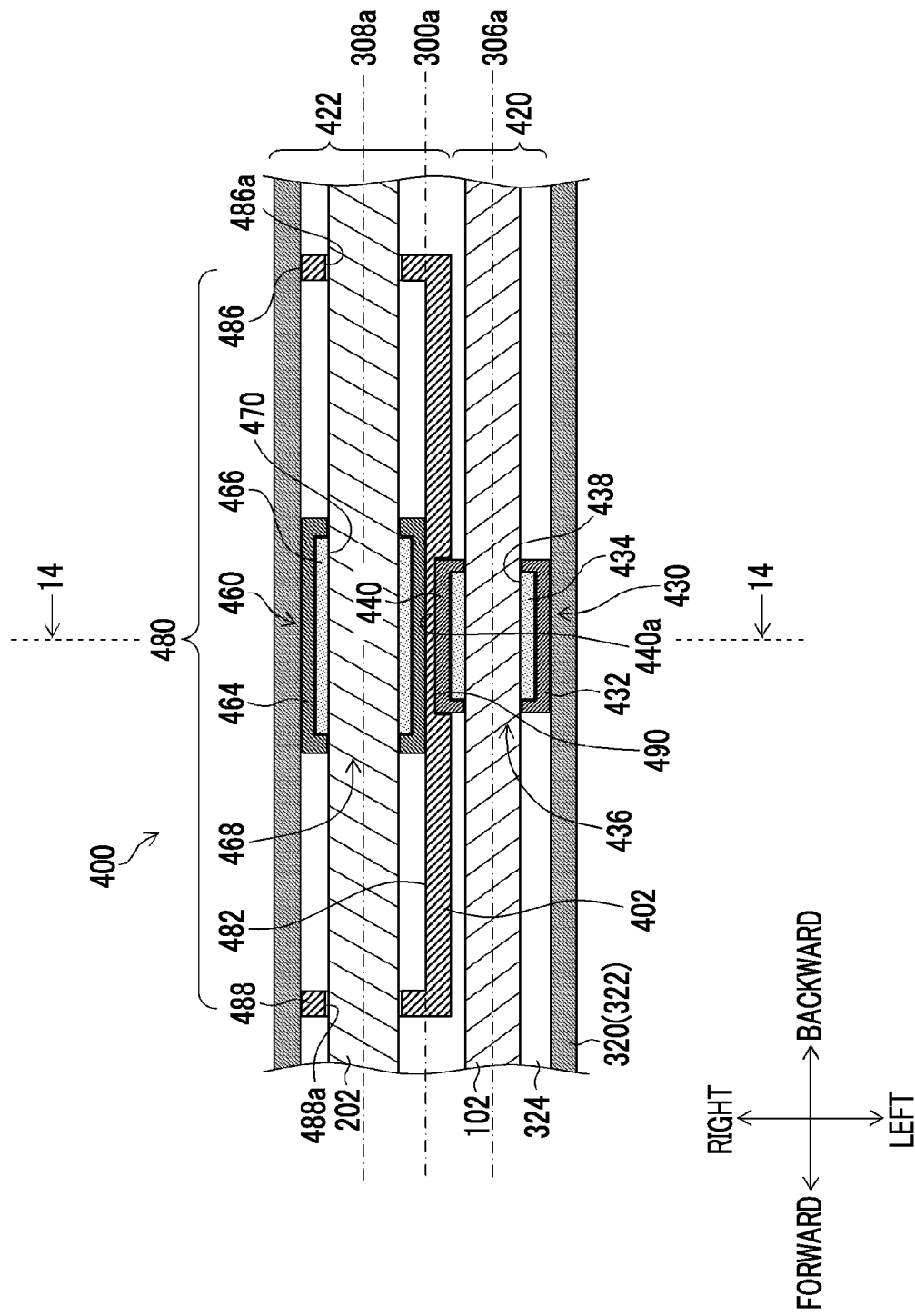
FIG. 11 is an enlarged view illustrating a portion of FIG. 9 in an enlarged manner.
Figure 12:
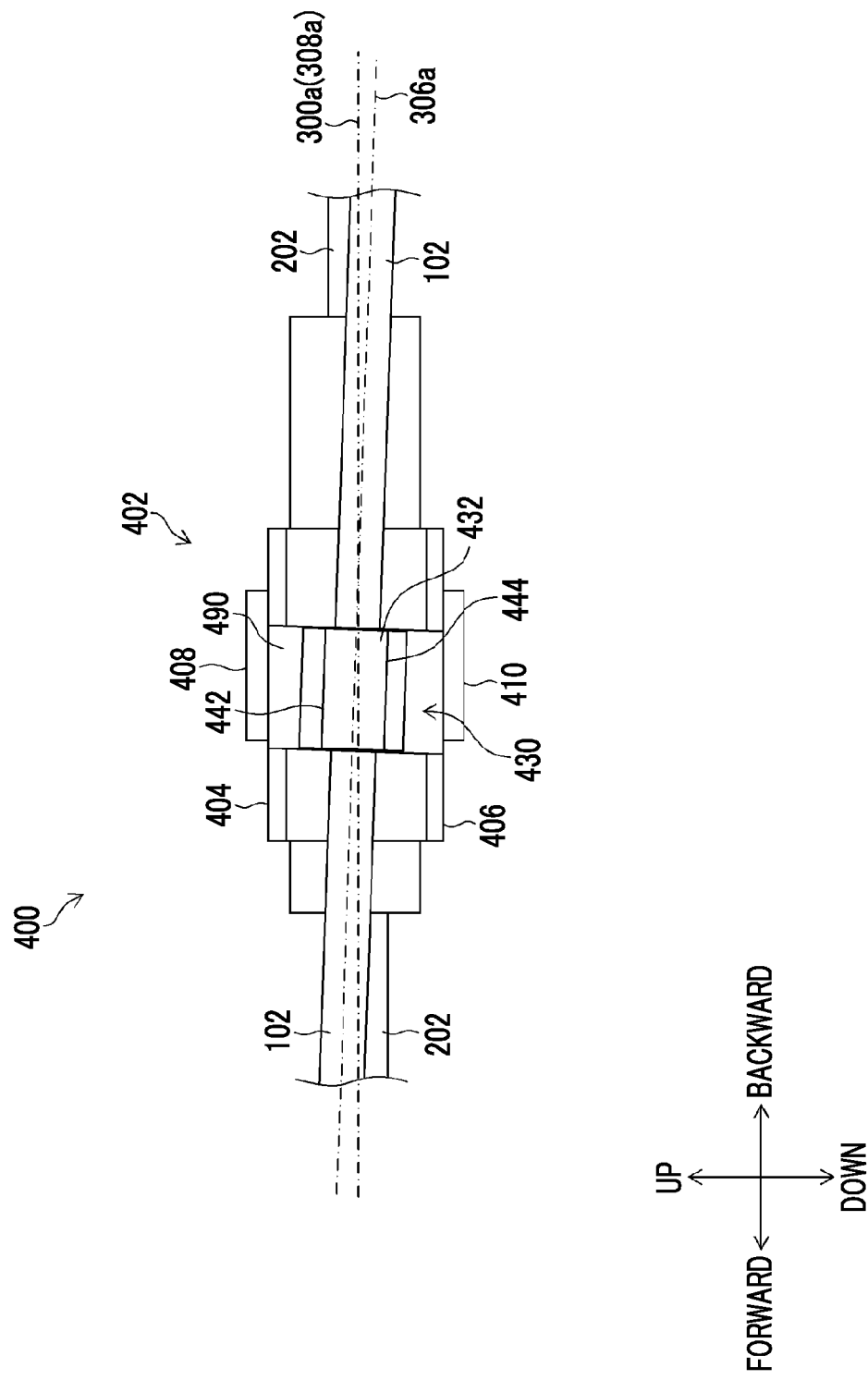
FIG. 12 is a left side view illustrating the slider from the left side.
Figure 13:
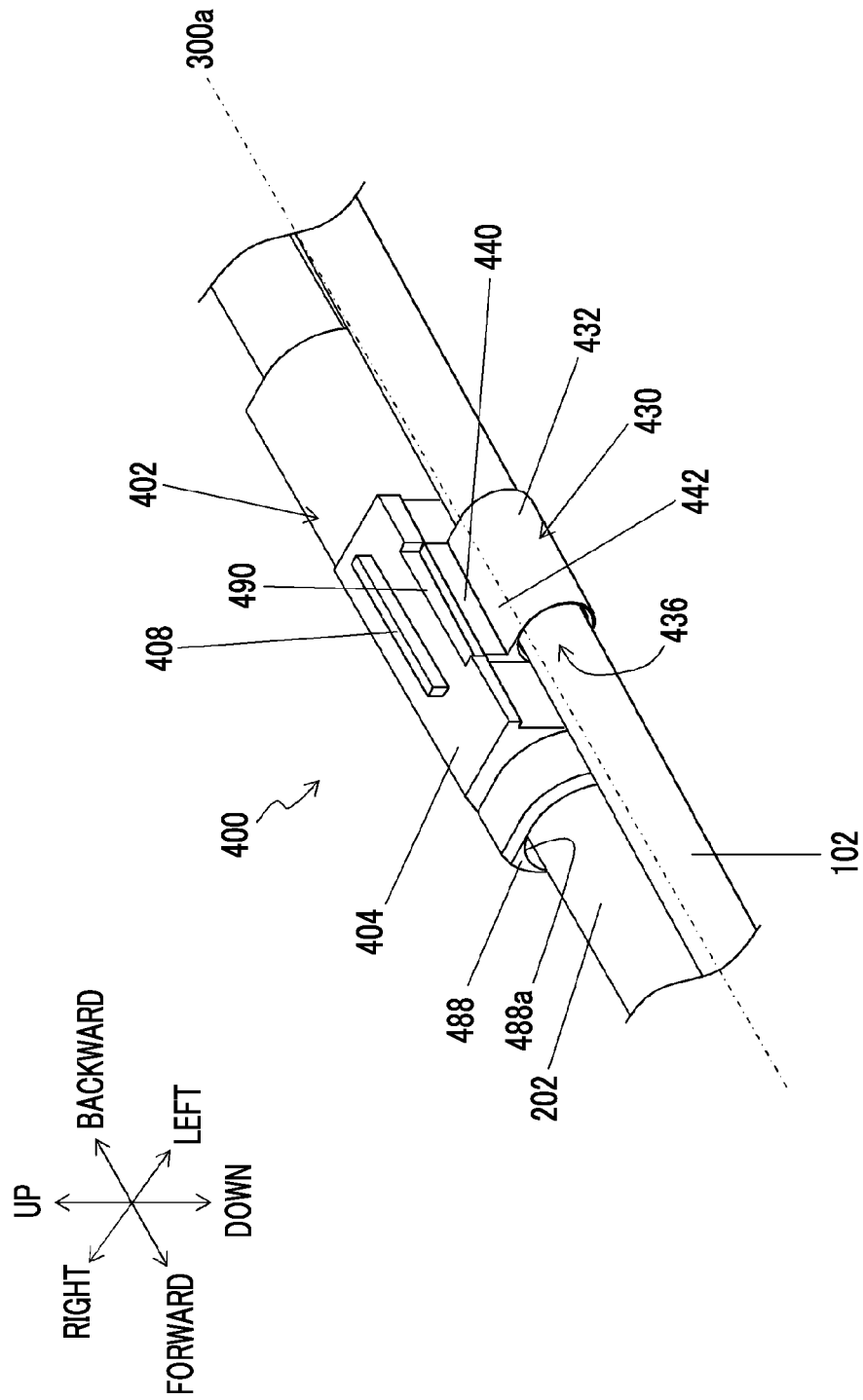
FIG. 13 is a perspective view obliquely illustrating the slider.
Figure 14:
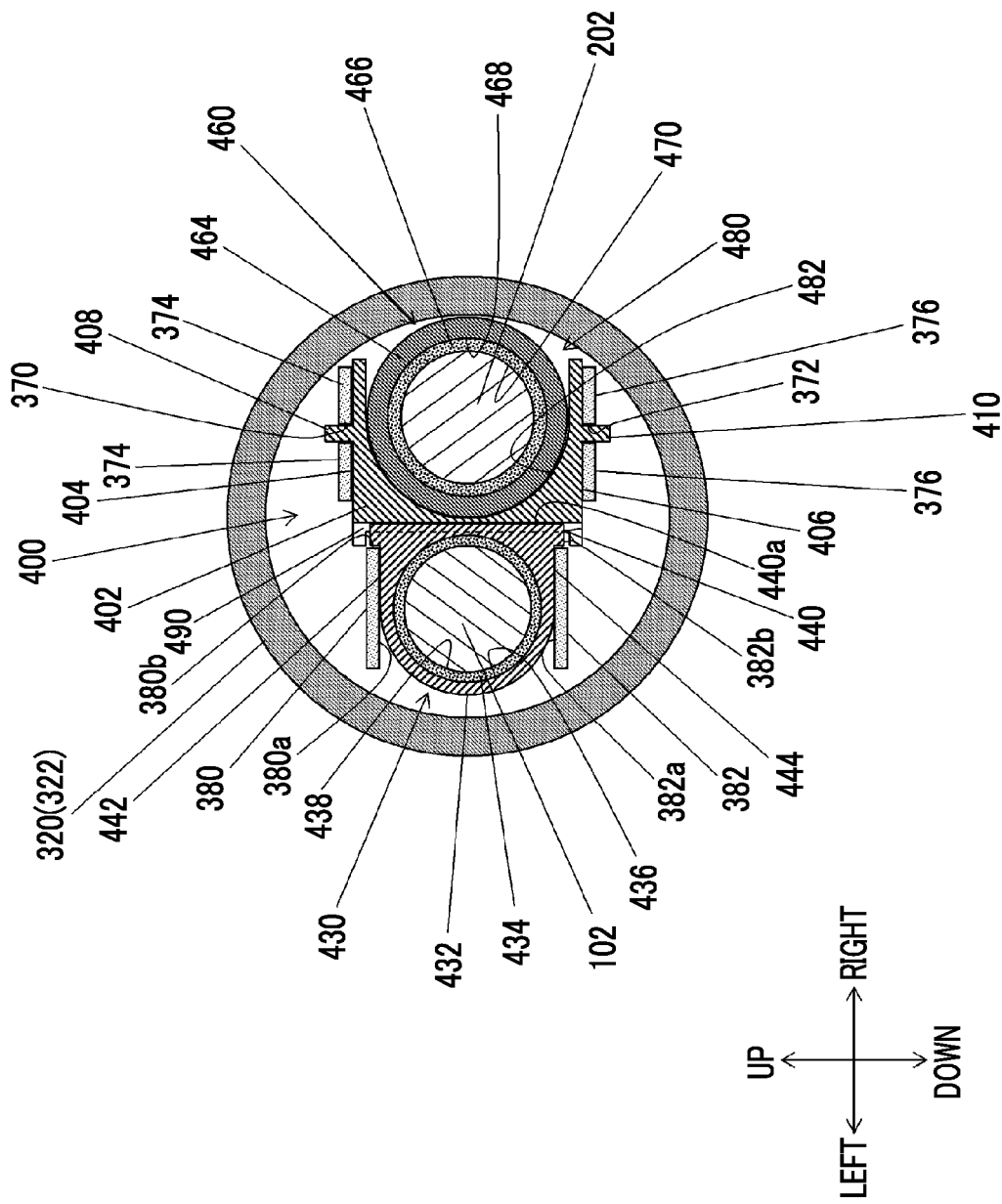
FIG. 14 is a sectional view when viewed from arrow 14-14 in FIG. 11.

FIG. 11 is an enlarged view illustrating a portion, in which the slider 400 is arranged in FIG. 9, in an enlarged manner, and FIGS. 12 and 13 are a left side view illustrating the slider 400 from the left side and a perspective view illustrating the slider from the front upper left side. FIG. 14 is a sectional view when viewed from arrow 14-14 in FIG. 11. In addition, FIGS. 11 to 14 illustrate a state where the endoscope insertion part 102 and the treatment tool insertion part 202 are inserted through the endoscope insertion passage 306 and the treatment tool insertion passage 308, respectively.

As illustrated in FIGS. 11 to 14, the slider 400 is formed of hard resins, metals, or the like, and has a slider body 402 to which components of the slider 400 is assembled.

The entire slider body 402, as illustrated in FIGS. 12 to 14, has a flat upper surface 404 and a flat lower surface 406, and has protruding strips 408 and 410, respectively, on the upper surface 404 and the lower surface 406.

The protruding strips 408 and 410 respectively protrude in the upward-downward direction at substantially central parts of the upper surface 404 and the lower surface 406 in a leftward-rightward direction, extend in the direction (forward-backward direction) of the reference axis 300a within the cavity part 324 of the overtube body 320, and are fitted into guide grooves 370 and 372 provided in an upper part and a lower part within the overtube body 320 as illustrated in FIG. 14.

The guide grooves 370 and 372 are respectively formed by gaps between a pair of left and right guide plates 374 and 374 and a pair of left and right the guide plates 376 and 376 that are arranged at the upper part and the lower part within the cavity part 324.

Figure 15:
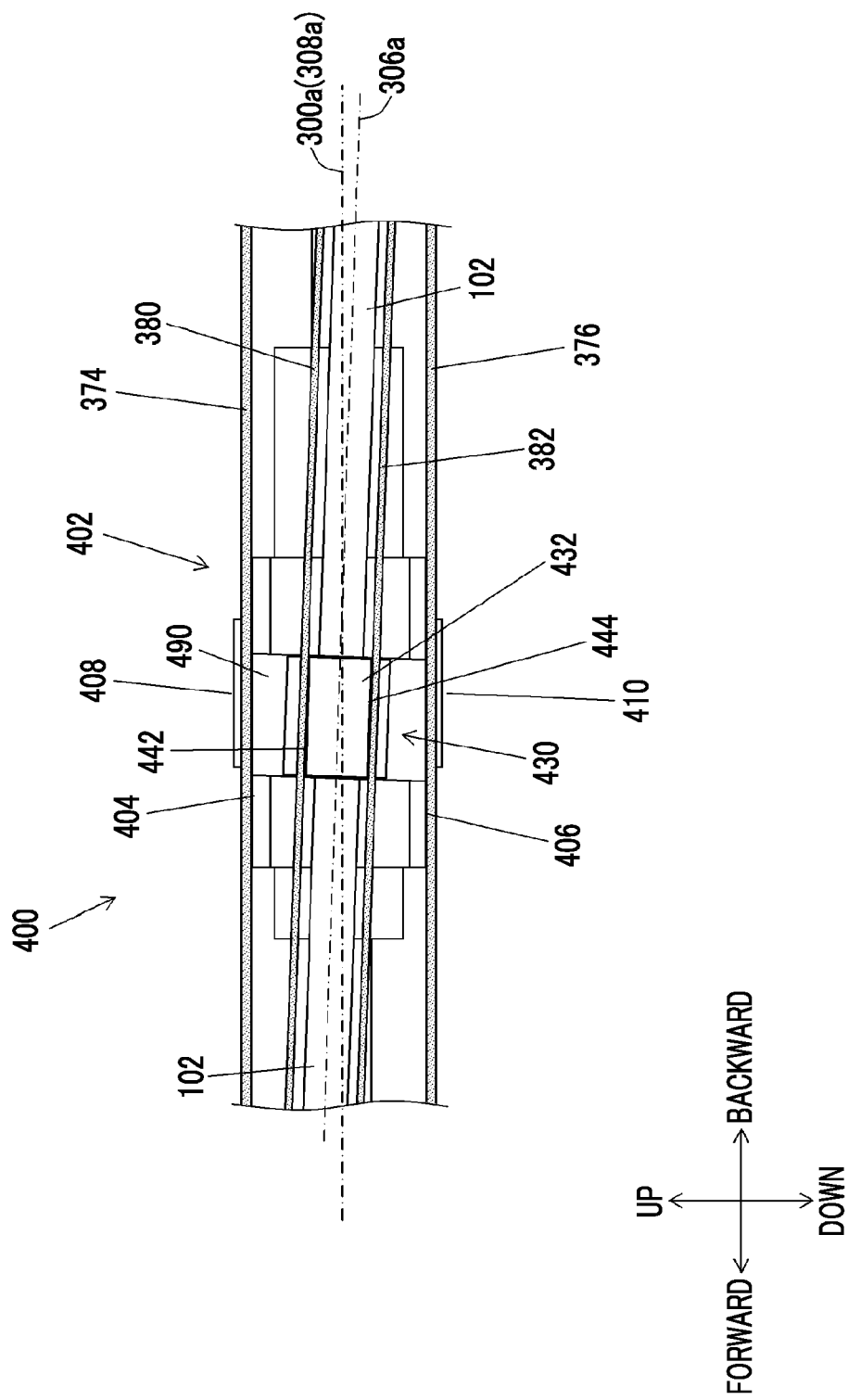
FIG. 15 is a left side view additionally illustrating a guide plate omitted in FIG. 12.
Figure 16:
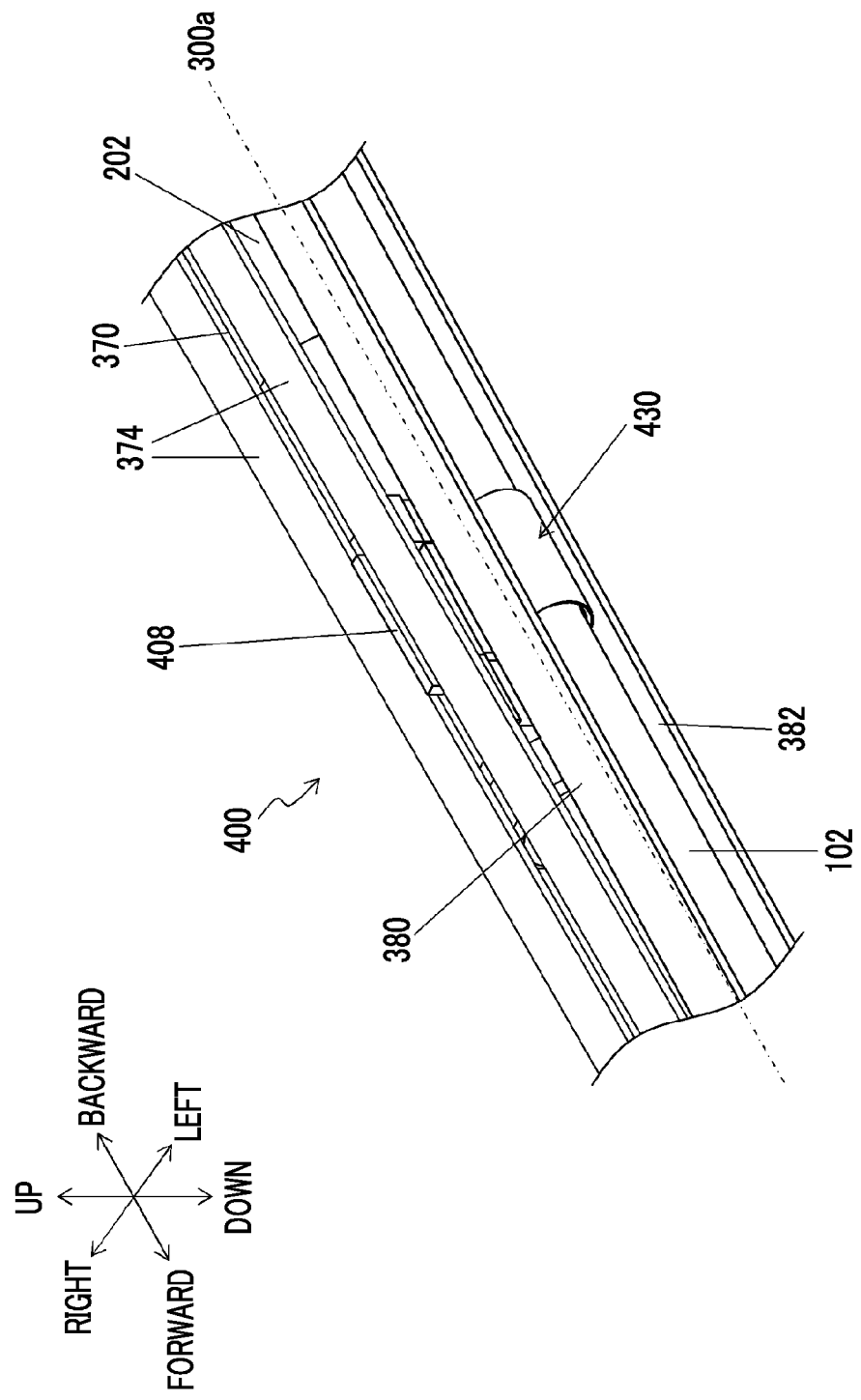
FIG. 16 is a perspective view additionally illustrating the guide plate omitted in FIG. 13.
Figure 17:
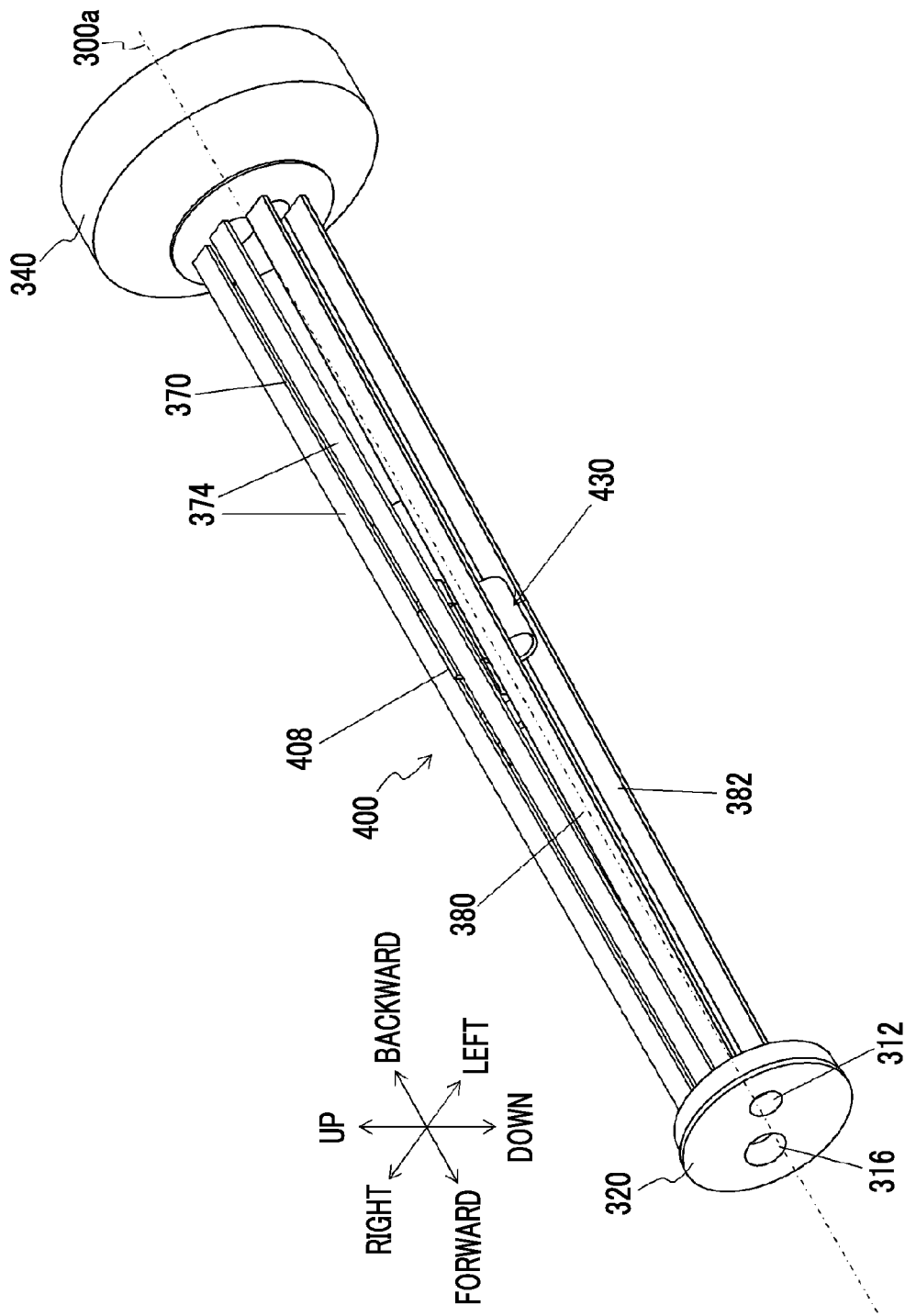
FIG. 17 is a perspective view of the overtube illustrated with only the overtube body omitted.

Although the guide plates 374 and 376 are omitted in FIGS. 12 and 13, as illustrated in perspective views of FIGS. 15 and 16 additionally illustrating the guide plates 374 and 376 and FIG. 17 illustrating the overtube 300 with only the overtube body 320 being omitted, the guide plates 374, 374, 376, and 376 are respectively formed in shape of a long plate, and are installed in the direction of the reference axis 300a (parallel to the reference axis 300a) by being stretched between the base end cap 340 and the distal end cap 360.

Accordingly, the guide grooves 370 and 372 are respectively arranged in the direction of the reference axis 300a from the base end cap 340 to the distal end cap 360 within the overtube body 320.

In a state where the slider body 402 is housed and arranged within the overtube body 320, the protruding strips 408 and 410 are respectively fitted into the guide grooves 370 and 372, and the upper surface 404 and the lower surface 406 respectively contact or approach the guide plates 374 and 374 and the guide plates 376 and 376. Accordingly, the slider body 402 is supported so as to be movable forward and backward in the forward-backward direction within the cavity part 324, and is supported in a state where the movement of the slider in the upward-downward direction and in the leftward-rightward direction and the rotation of the slider in all directions (the rotation of the slider around three axes including a forward-backward axis, a leftward-rightward axis, and an upward-downward direction) are restricted.

In addition, the guide grooves 370 and 372 may not be formed by the guide plates 374 and 374 and the guide plates 376 and 376 arranged within the cavity part 324 of the overtube body 320, and may be formed in the outer wall 322 of the overtube body 320 or may be formed by other configurations.

Additionally, a range (movable range) in which the slider body 402 moves forward and backward in the forward-backward direction with respect to the overtube body 320 is a movable range of the slider 400, and a range having a position where the slider body 402 abuts against the base end cap 340 as a rear end and having a position where the slider body abuts against the distal end cap 360 as a front end. However, the rear end and the front end of the movable range of the slider 400 may not be restricted by the base end cap 340 and the distal end cap 360.

Additionally, the slider 400, as illustrated in FIG. 11, has a left endoscope-coupled part 420 that is coupled (engaged) with the endoscope insertion part 102, and a right treatment tool-coupled part 422 that is coupled (engaged) with the treatment tool insertion part 202.

The endoscope-coupled part 420 is a left region of the slider 400, is provided on the left of the slider body 402, and has an endoscope-coupled member 430 that is coupled with the endoscope insertion part 102.

Figure 19:
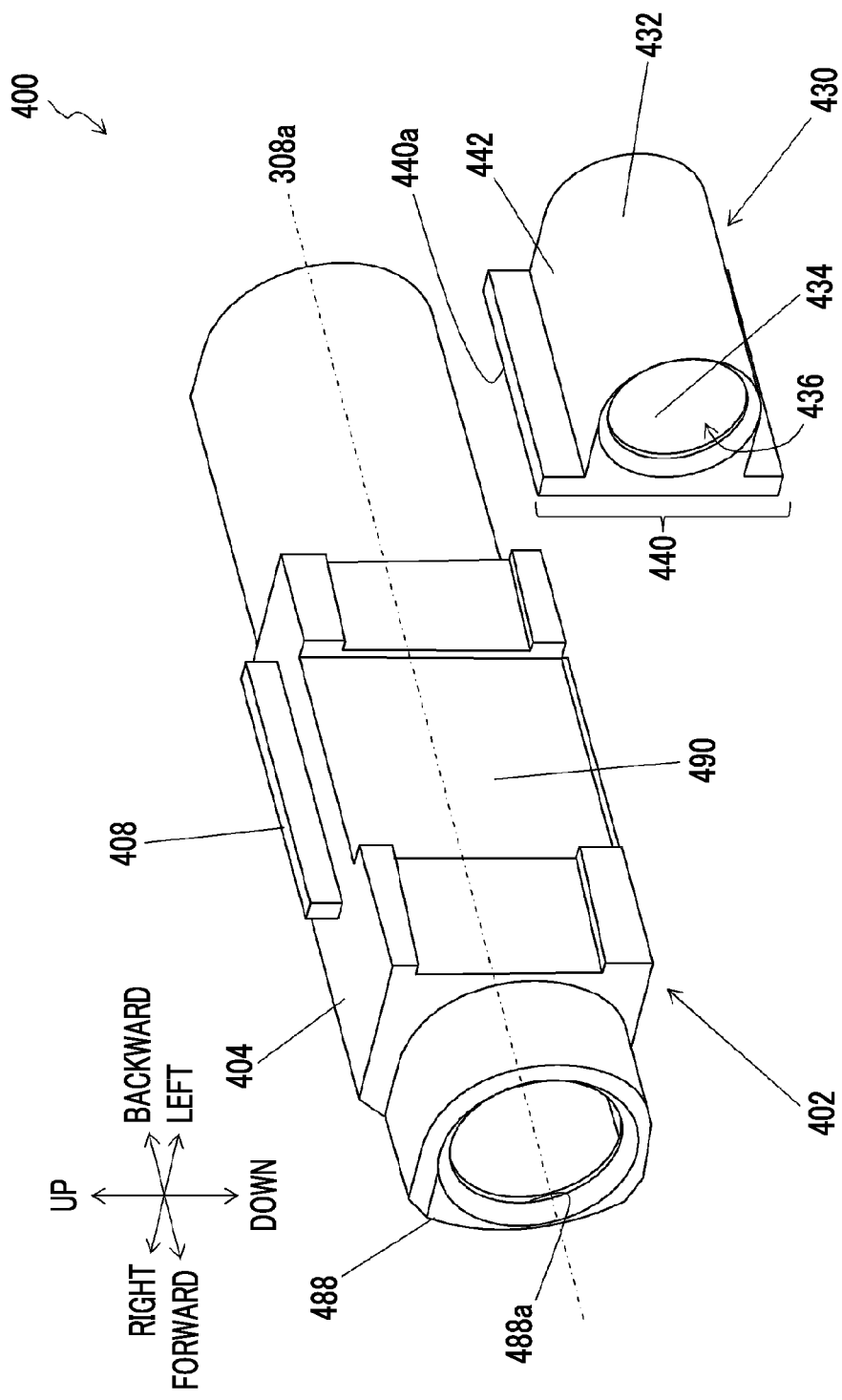
FIG. 19 is a perspective view illustrating the slider from the front upper left side.

The endoscope-coupled member 430 consists of a frame body 432 that forms an outer wall, and a pressure-contact member 434 arranged inside the frame body 432, as illustrated in FIGS. 11 and 14 and a perspective views of FIG. 19 illustrated while being separated from the slider body 402.

The frame body 432 is integrally formed of hard resins, metals, or the like, and has a through-hole 436 that penetrates in the forward-backward direction, as a through-hole of the endoscope-coupled member 430. The through-hole 436 has at least a greater diameter than the external diameter of the endoscope insertion part 102, and a central axis of the through-hole 436 is arranged coaxially with the endoscope insertion axis 306a in the oblique direction with reference to the reference axis 300a as will be described below. This secures a space that serves as the endoscope insertion passage 306 within the overtube body 320.

The pressure-contact member 434 is formed in a cylindrical shape using elastic materials, such as elastic rubber, and has a through-hole 438 that penetrates in the forward-backward direction. The pressure-contact member 434 is inserted into the through-hole 436 of the endoscope-coupled member 430 (frame body 432), and is fixed to the frame body 432.

The through-hole 438 of the pressure-contact member 434 has a slightly smaller diameter than the external diameter of the endoscope insertion part 102, and a central axis of the through-hole 438 is arranged substantially coaxially with the central axis of the through-hole 436 of the frame body 432.

Therefore, when the endoscope insertion part 102 is inserted through the endoscope insertion passage 306, as illustrated in FIGS. 11 and 14, the endoscope insertion part 102 is inserted through the through-hole 436 of the endoscope-coupled member 430 and is inserted through the through-hole 438 of the pressure-contact member 434 of which the diameter is increased due to elastic deformation, and the pressure-contact member 434 is brought into pressure contact with the endoscope insertion part 102. Accordingly, a frictional force is generated with respect to the relative movement between the endoscope insertion part 102 and the pressure-contact member 434, and unless a greater external force than the frictional force is applied between the endoscope insertion part 102 and the pressure-contact member 434, and the endoscope insertion part 102 and the endoscope-coupled member 430 are brought into a state where they are coupled (engaged) in an interlockable manner via the pressure-contact member 434.

The pressure-contact member 434 is one form of a constituent member that constitutes an endoscope engagement part that is engaged with the endoscope insertion part 102 in the slider 400.

Additionally, as illustrated in FIGS. 11, 14, and 19, a guide part 440 that has a flat quadrangular guide surface 440a as a right side surface and extends in the upward-downward direction is formed as a guide projection in a right portion of the frame body 432 of the endoscope-coupled member 430. The guide part 440 is fitted into a groove 490 serving as a guide groove that has a flat bottom surface provided within the overtube body 320 in a left side surface of the slider body 402. Accordingly, the endoscope-coupled member 430 is engaged with the overtube body 320 so as to be movable in the upward-downward direction, while the movement thereof in the forward-backward direction with respect to the overtube body 320 is restricted. That is, the slider body 402 and the endoscope-coupled member 430 are engaged with each other so as to move integrally with the forward and backward movement in the forward-backward direction.

In addition, the groove 490 may slide the guide part 440 in a direction having a movement component at least perpendicular to the reference axis 300a.

Meanwhile, a flat upper surface 442 and a flat lower surface 444 that perpendicularly intersect the guide surface 440a of the guide part 440 as illustrated in FIGS. 14 and 19 and are parallel to the central axis of the through-hole 436 are formed in a left portion of the guide part 440 of the endoscope-coupled member 430. The upper surface 442 and the lower surface 444 of the frame body 432 are arranged between two guide plates 380 and 382 disposed as illustrated in FIGS. 15 to 17 within the overtube body 320, and contact or approach guide surfaces 380a and 382a of the guide plates 380 and 382. This restricts the movement of the endoscope-coupled member 430 in the upward-downward direction.

Additionally, as illustrated in FIG. 14, when side surfaces 380b and 382b of the guide plates 380 and 382 contact or approach portions that protrudes in the upward-downward direction of the guide part 440 of the endoscope-coupled member 430, the movement of the endoscope-coupled member 430 in the leftward-rightward direction is also restricted, so that the guide part 440 is not prevented from coming off the groove of the slider body 402.

The guide plates 380 and 382, as illustrated in FIGS. 15 to 17, are formed in the shape of a long plate, and are arranged within the overtube body 320 by being stretched between the base end cap 340 and the distal end cap 360.

Figure 18:
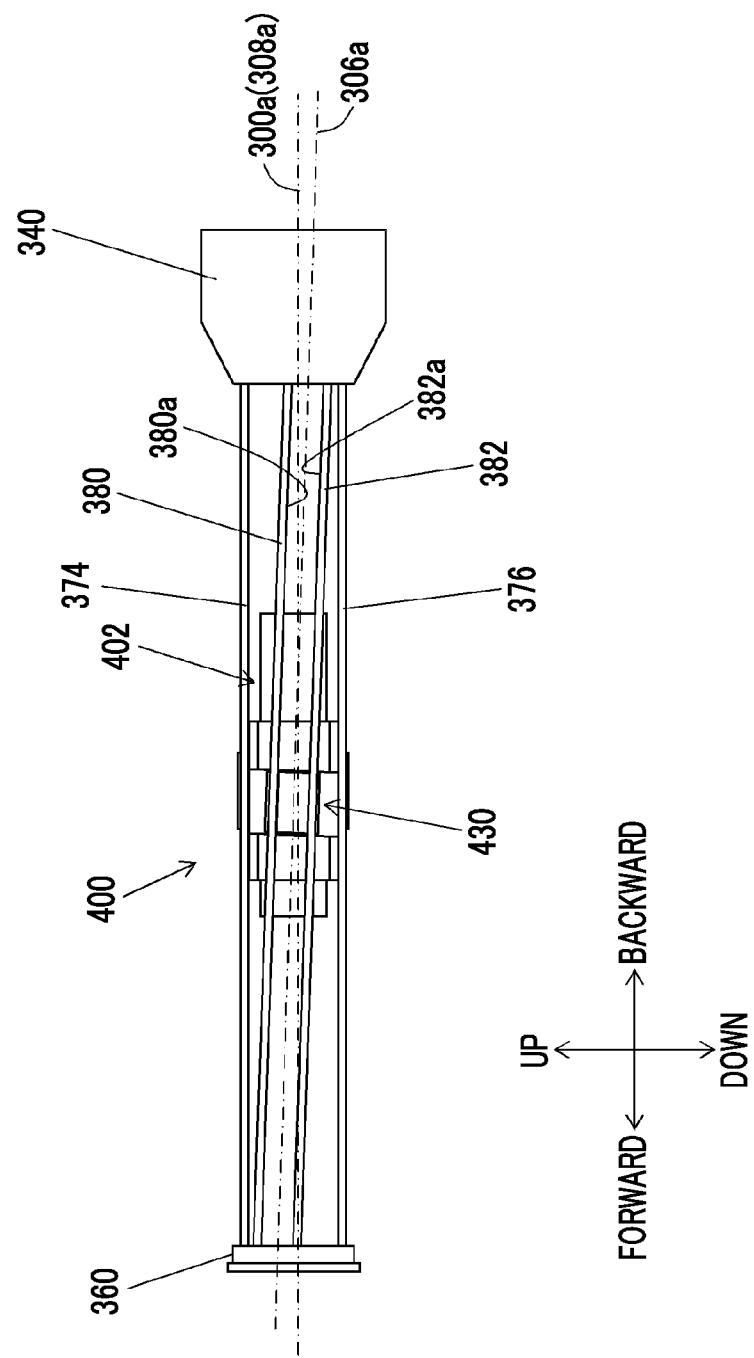
FIG. 18 is a left side view illustrating FIG. 17 from the left side.

Additionally, the guide plates 380 and 382, as illustrated also in a left side view of FIG. 18, are arranged at upper and lower positions between which the endoscope insertion axis 306a is sandwiched in the direction of the oblique endoscope insertion axis 306a that is oblique to the reference axis 300a, and the guide surfaces 380a and 382a of the guide plates 380 and 382 are arranged so as to be orthogonal the vertical reference plane.

Accordingly, the endoscope-coupled member 430 is guided by the guide plates 380 and 382 and displaced in the upward-downward direction, with respect to the forward and backward movement in the forward-backward direction within the overtube body 320, and is moved in the direction of the endoscope insertion axis 306a. That is, the central axis of the through-hole 436 of the endoscope-coupled member 430 is always arranged coaxially (the same position and direction) with the endoscope insertion axis 306a that has the oblique direction with respect to the reference axis 300a, irrespective of the position, in the forward-backward direction, of the slider 400 within the overtube body 320.

Therefore, even in a case where the endoscope insertion axis 306a is configured so as to become the oblique direction with respect to the reference axis 300a (treatment tool insertion axis 308a) as in the present embodiment, It is possible to move the endoscope-coupled member 430 (slider 400) forward and backward in the forward-backward direction, that is, to move the endoscope insertion part 102 forward and backward in the direction of the endoscope insertion axis 306a, without changing the insertion position of the endoscope insertion part 102 in the overtube 300.

In addition, since the coupling herein is based on the elastic force of the pressure-contact member 434, the engagement position (a position where the slider 400 is engaged in the endoscope insertion part 102) of the endoscope insertion part 102 coupled to the endoscope-coupled member 430 (slider 400) can be arbitrarily adjusted.

The treatment tool-coupled part 422 coupled with the treatment tool insertion part 202 in the slider 400, as illustrated in FIGS. 11 to 14, is provided in the slider body 402 in a right region of the slider 400. The treatment tool-coupled part 422, as illustrated in perspective views of the slider 400 of FIGS. 11, 14, and 20, includes a sleeve 460 coupled to the treatment tool insertion part 202, and a guide part 480 that guides the sleeve 460 so as to be movable forward and backward in the direction (forward-backward direction) of the treatment tool insertion axis 308a.

The sleeve 460 is housed in a space of the guide part 480, is supported so as to be movable forward and backward in the forward-backward direction, and consists of a sleeve body (frame body) 464 that forms an outer wall, and a pressure-contact member 466 arranged inside the sleeve body 464.

The sleeve body 464 is formed in a cylindrical shape using hard resins, metals, or the like, and has a through-hole 468, which penetrates in the forward-backward direction, as a through-hole of the sleeve 460.

The through-hole 468 has at least a greater diameter than the external diameter of the treatment tool insertion part 202, and secures a space, which serves as the treatment tool insertion passage 308, within the overtube body 320 by arranging a central axis of the through-hole 468 coaxially with the treatment tool insertion axis 308a.

The pressure-contact member 466 is formed in a cylindrical shape using elastic materials, such as elastic rubber, and has a through-hole 470 that penetrates in the forward-backward direction. The pressure-contact member 466 is inserted into the through-hole 468 of the sleeve 460 (sleeve body 464), and is fixed to the sleeve body 464.

The through-hole 470 of the pressure-contact member 466 has a slightly smaller diameter than the external diameter of the treatment tool insertion part 202, and a central axis of the through-hole 470 is arranged substantially coaxially with the central axis of the through-hole 468 of the sleeve 460.

Therefore, when the treatment tool insertion part 202 is inserted through the treatment tool insertion passage 308, as illustrated in FIGS. 11 and 14, the treatment tool insertion part 202 is inserted through the through-hole 468 of the sleeve 460 and is inserted through the through-hole 470 of the pressure-contact member 466 of which the diameter is increased due to elastic deformation, and the pressure-contact member 466 is brought into pressure contact with the treatment tool insertion part 202. Accordingly, a frictional force is generated with respect to the relative movement between the treatment tool insertion part 202 and the pressure-contact member 466, and unless a greater external force than the frictional force is applied between the treatment tool insertion part 202 and the pressure-contact member 466, the treatment tool insertion part 202 and the sleeve 460 are brought into a state where they are coupled (engaged) in an interlockable manner via the pressure-contact member 466.

The pressure-contact member 466 is one form of the constituent member that constitutes a treatment tool engagement part that is engaged with the treatment tool insertion part 202 in the slider 400.

In addition, since the coupling between the treatment tool insertion part 202 and the sleeve 460 herein is based on the elastic force of the pressure-contact member 466, the engagement position (a position where the sleeve 460 is engaged in the treatment tool insertion part 202) of the treatment tool insertion part 202 coupled to the sleeve 460 can be arbitrarily adjusted.

Figure 20:
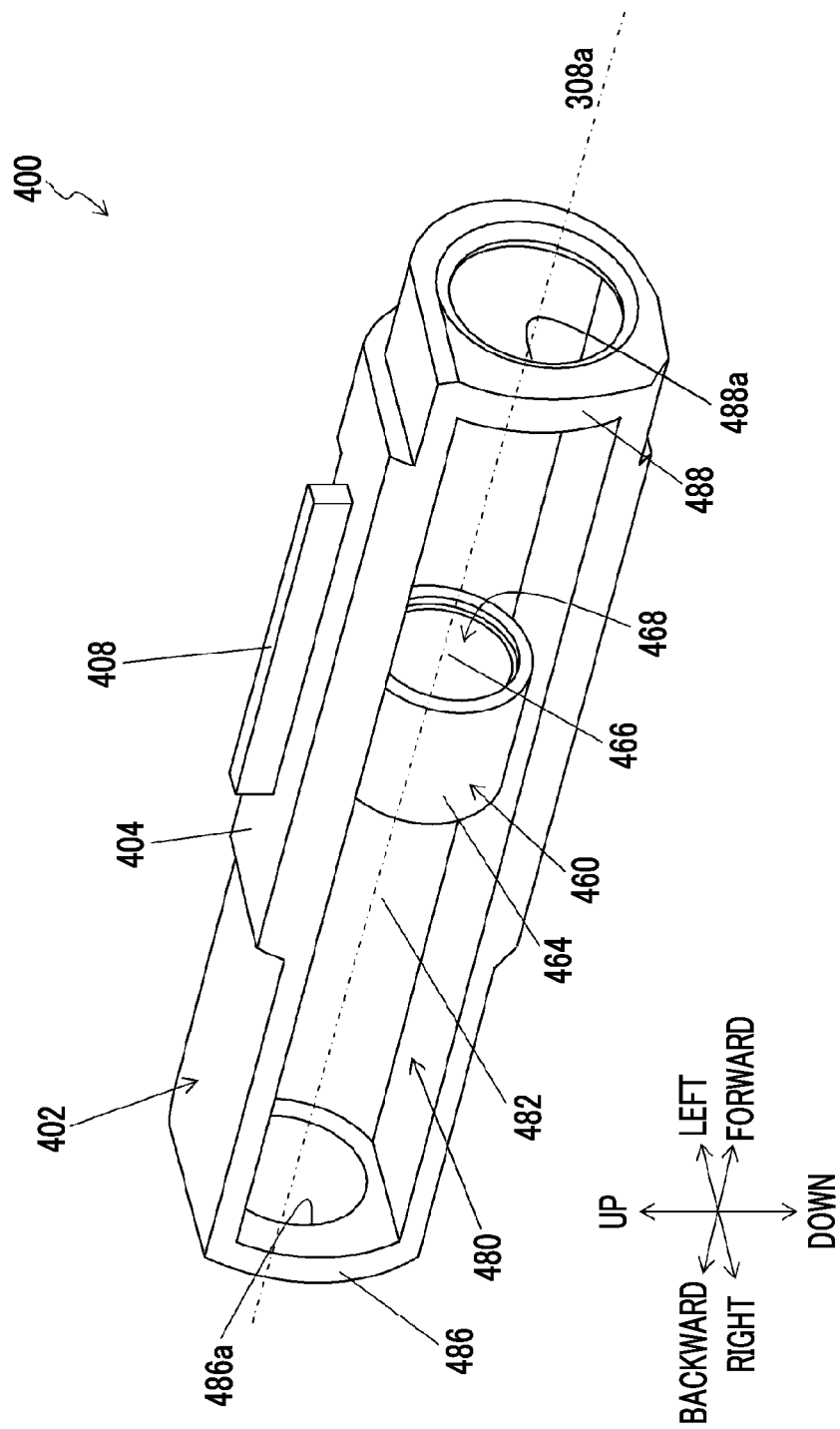
FIG. 20 is a perspective view illustrating the slider from the front upper right side.

Meanwhile, the guide part 480 of the treatment tool-coupled part 422, as illustrated in FIGS. 11, 14, and 20, is formed by a space surrounded by a guide surface 482 of the slider body 402 that extends in the direction of the treatment tool insertion axis 308a (reference axis 300a) within the overtube body 320, and an inner peripheral surface (an inner peripheral surface of the outer wall 322) of the overtube body 320.

The guide surface 482 is curved in a U-shape toward an opening in a section orthogonal to the reference axis 300a, and as illustrated in FIG. 14, the inner peripheral surface of the overtube body 320 (outer wall 322) is arranged so as to face the opening of the guide surface 482, within the cavity part 324 of the overtube body 320.

Accordingly, the space surrounded by the guide surface 482 and the inner peripheral surface of the overtube body 320 is formed as a space of the guide part 480. The space of the guide part 480 is formed at a position where the treatment tool insertion axis 308a is inserted therethrough, and extends along the treatment tool insertion axis 308a.

The sleeve 460 is housed and arranged in the guide part 480 as described above, and the central axis (the central axis of the through-hole 468) of the sleeve 460 is arranged coaxially with the treatment tool insertion axis 308a. In the guide part 480, an outer peripheral surface of the sleeve 460 contacts or approaches the guide surface 482 and the inner peripheral surface of the overtube body 320.

Accordingly, in the guide part 480, the sleeve 460 is supported so as to be movable in the forward-backward direction and rotatable around its axis, and is supported in a state where the movement of the sleeve in the upward-downward direction and in the leftward-rightward direction is restricted.

Additionally, a base end and a distal end of the guide part 480 (slider body 402), as illustrated in FIGS. 11 and 20, are provided with a rear end 486 and a front end 488 having openings 486a and 488a through which the treatment tool insertion part 202 is insertable.

The rear end 486 and the front end 488 abut against the end of the sleeve 460 to restrict the movement of the sleeve 460 in the forward-backward direction, when the sleeve 460 arranged in the guide part 480 moves forward and backward in the forward-backward direction.

Therefore, a range (movable range) where the sleeve 460 moves forward and backward in the forward-backward direction with respect to the slider body 402 is limited with a position where the sleeve abuts against the rear end 486 being defined as a rear end and a position where the sleeve abuts against the front end 488 being defined as a front end. However, the rear end and the front end of the movable range of the sleeve 460 may not be restricted by the rear end 486 and the front end 488 of the present embodiment.

In addition, in the present embodiment, the space of the guide part 480 is formed by the guide surface 482 of the slider body 402 and the inner peripheral surface of the overtube body 320. Therefore, as compared to a configuration in which the guide part 480 is formed only by the slider body 402 and the sleeve 460 is completely housed inside the slider body 402, the slider body 402 is downsized, and the external diameter of the overtube body 320 is also made smaller along with this downsizing. However, the invention is not limited to this configuration, and a configuration in which the pressure-contact member 460 is completely housed inside the slider body 402 may be adopted.

The operation of the slider 400 configured as described above will be described.

If the endoscope insertion part 102 is inserted through the endoscope insertion passage 306 of the overtube 300, the endoscope insertion part 102 and the endoscope-coupled member 430 of the slider 400 are coupled together, and if the treatment tool insertion part 202 is inserted through the treatment tool insertion passage 308 of the overtube 300, the treatment tool insertion part 202 and the sleeve 460 are coupled together.

In these tasks, even before the endoscope insertion part 102 is inserted through the endoscope insertion passage 306, the central axis of the through-hole 436 of the endoscope-coupled member 430 is arranged coaxially (the same position and the same direction) with the endoscope insertion axis 306a by the endoscope-coupled member 430 being guided by the guide plates 380 and 382. Therefore, by obliquely inserting the endoscope insertion part 102 in the direction of the through-hole 342 of the base end cap 340 from the endoscope insertion port 310 (that is, inserting the endoscope insertion part in the direction of the endoscope insertion axis 306a that is oblique to the reference axis 300a), the endoscope insertion part 102 can be easily inserted through the through-hole 436 of the endoscope-coupled member 430 even if the slider 400 is at any position in the forward-backward direction within the overtube body 320.

Similarly, since the central axis of the through-hole 468 of the sleeve 460 is always arranged coaxially with the treatment tool insertion axis 308a by being guided by the guide part 480 of the slider body 402, the treatment tool insertion part 202 can be easily inserted through the through-hole 468 of the sleeve 460

Figure 21:
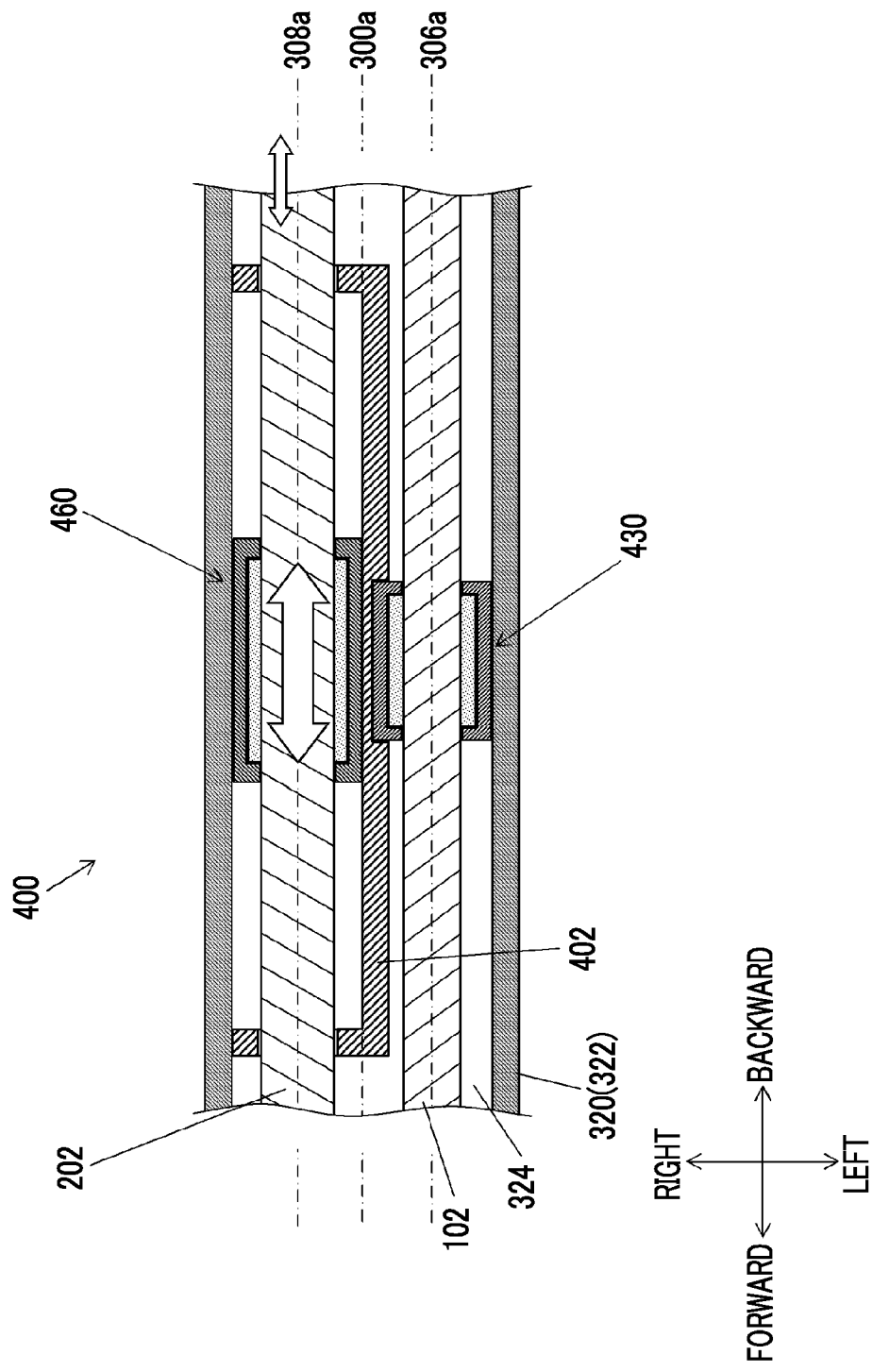
FIG. 21 is an explanatory view and a horizontal sectional view used for the description of the action of the slider.

As illustrated in FIG. 21, it is supposed that a surgeon performs a forward and backward movement operation for moving the treatment tool insertion part 202 forward and backward in the axial direction (forward-backward direction) in a state where the sleeve 460 has not reached any of the rear end and the front end of the movable range thereof with respect to the slider body 402 (guide part 480).

In this case, in a case where the sleeve 460 has moved forward and backward within the movable range thereof with respect to the slider body 402, the slider body 402 does not move with respect to the forward and backward movement of the treatment tool insertion part 202.

Therefore, a forward and backward movement operation in the dead zone where the endoscope insertion part 102 does not interlock with the forward and backward movement of the treatment tool insertion part 202 is performed.

Figure 22:
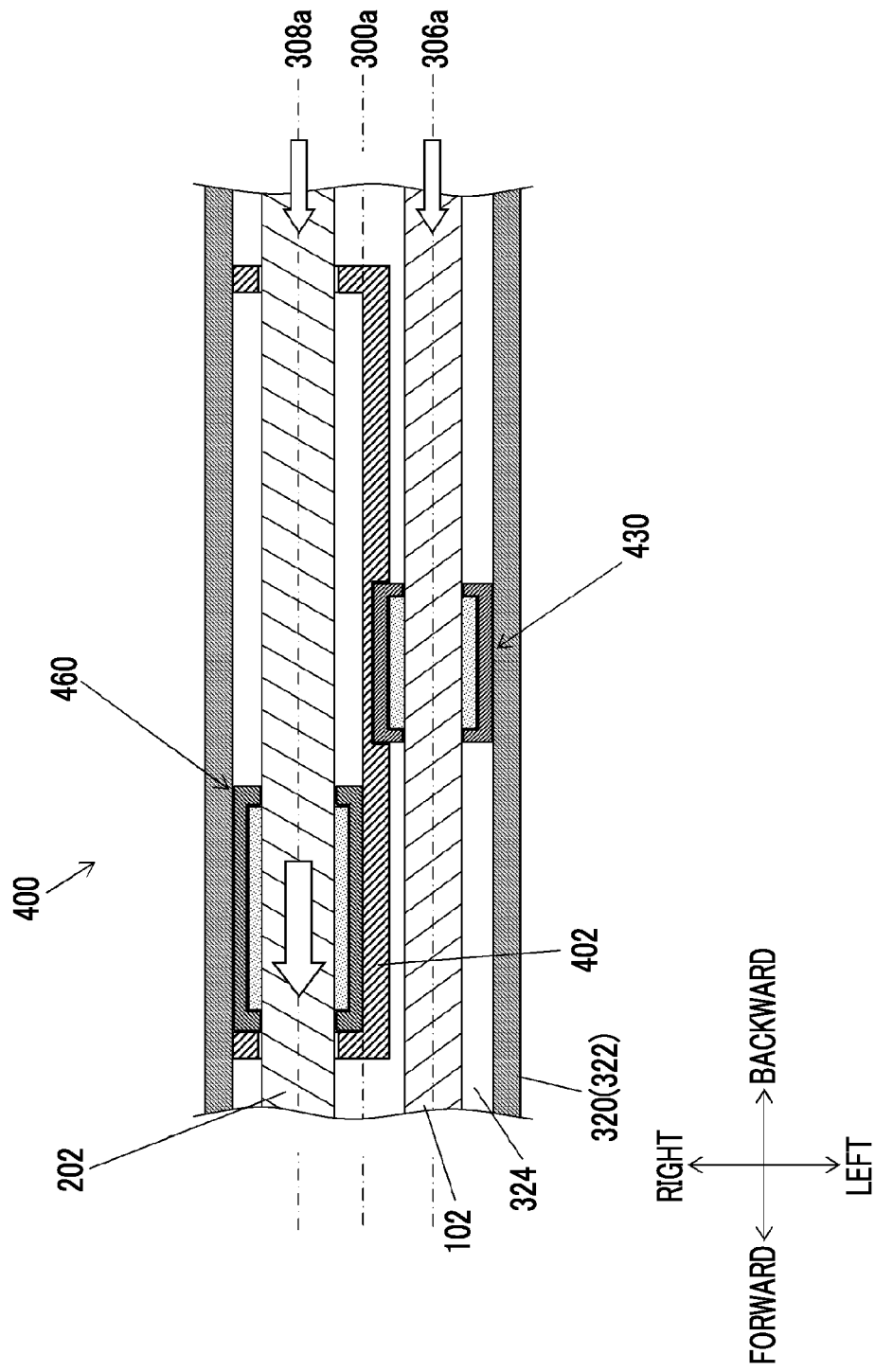
FIG. 22 is an explanatory view and a horizontal sectional view used for the description of the action of the slider.

Meanwhile, as illustrated in FIG. 22, if the treatment tool insertion part 202 is operated to move forward in a state where the sleeve 460 reaches the front end of the movable range thereof with respect to the slider body 402, the sleeve 460 and the slider body 402 move forward with respect to the overtube body 320 together with the treatment tool insertion part 202. Then, the endoscope-coupled member 430 coupled with the endoscope insertion part 102 also moves forward together with the slider body 402.

Accordingly, the endoscope insertion part 102 also moves forward, and the endoscope insertion part 102 moves forward in an interlocking manner with the treatment tool insertion part 202. That is, a forward movement operation in the sensing zone where the endoscope insertion part 102 interlocks with the forward movement of the treatment tool insertion part 202 is performed.

Additionally, in the case of such a forward movement operation in the sensing zone, the endoscope-coupled member 430 not only moves forward together with the slider body 402, but also moves in an upward direction with respect to the slider body 402 through the guiding of the guide plates 380 and 382, and moves in the direction of the endoscope insertion axis 306*a*.

Figure 24:
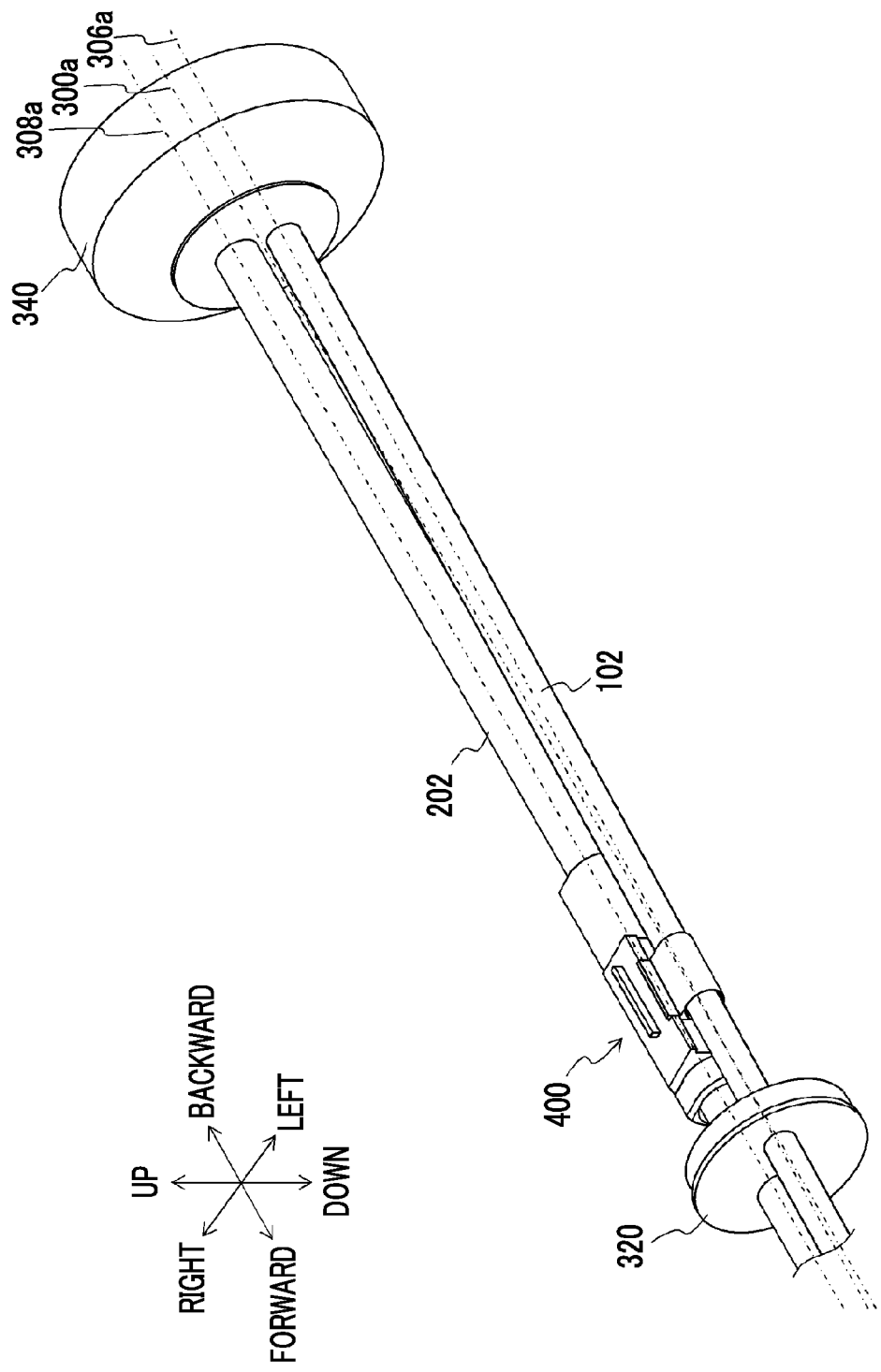
FIG. 24 is an explanatory view and a perspective view used for the description of the action of the slider.

For example, as illustrated in the perspective view of FIG. 10 as described above, and the sectional view of FIG. 14, the slider 400 moves forward as illustrated in a perspective view of FIG. 24, in a case where the forward movement operation in the sensing zone is performed, in a state where the slider 400 has not reached any of the rear end and the front end of the movable range thereof with respect to the overtube body 320. In this case, the endoscope-coupled member 430 moves forward together with the slider body 402, and as illustrated also in a sectional view of FIG. 26, moves in the upward direction, thereby moving in the direction of the endoscope insertion axis 306*a*.

Figure 23:
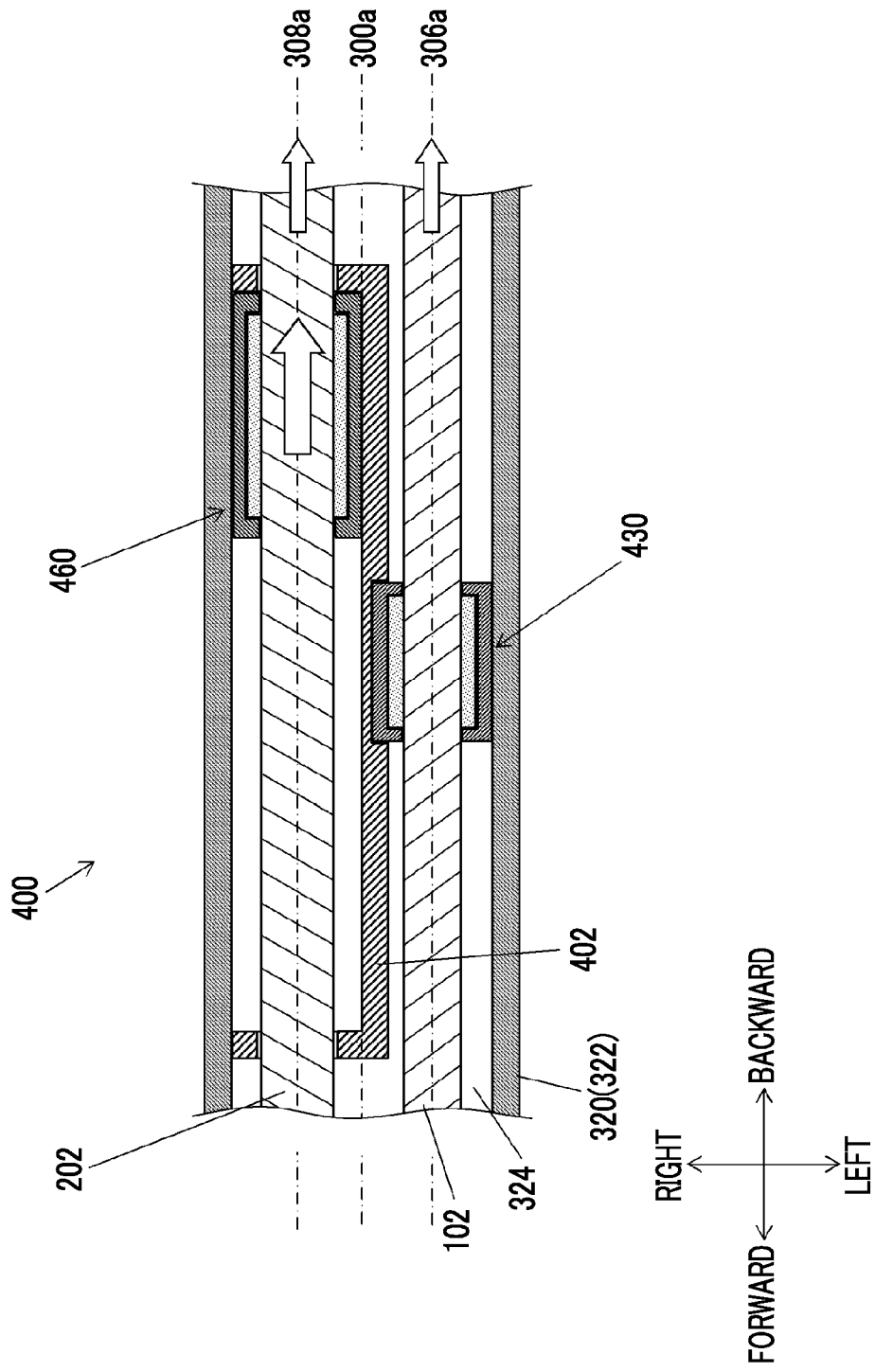
FIG. 23 is an explanatory view and a horizontal sectional view used for the description of the action of the slider.

Similarly, as illustrated in FIG. 23, if the treatment tool insertion part 202 is operated to move backward in a state where the sleeve 460 reaches the rear end of the movable range thereof with respect to the slider body 402, the sleeve 460 and the slider body 402 move backward with respect to the overtube body 320 together with the treatment tool insertion part 202. Then, the endoscope-coupled member 430 coupled with the endoscope insertion part 102 also moves backward together with the slider body 402.

Accordingly, the endoscope insertion part 102 also moves backward, and the endoscope insertion part 102 moves backward in an interlocking manner with the treatment tool insertion part 202. That is, a backward movement operation in the sensing zone where the endoscope insertion part 102 interlocks with the backward movement of the treatment tool insertion part 202 is performed.

Additionally, even in the case of such a backward movement operation in the sensing zone, the endoscope-coupled member 430 not only moves backward together with the slider body 402, but also moves in a downward direction with respect to the slider body 402 through the guiding of the guide plates 380 and 382, and moves in the direction of the endoscope insertion axis 306*a*.

Figure 25:
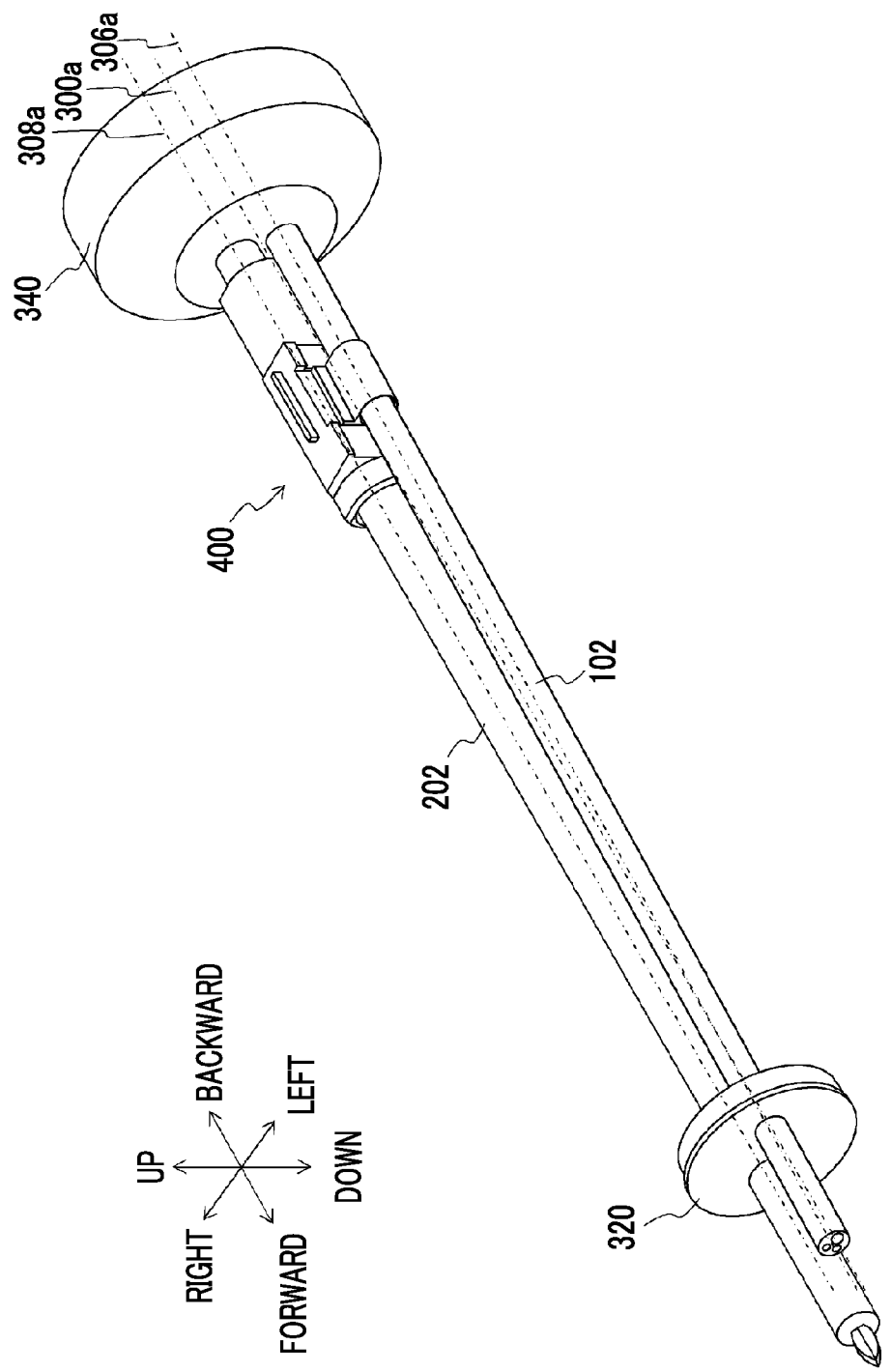
FIG. 25 is an explanatory view and a perspective view used for the description of the action of the slider.

For example, as illustrated in the perspective view of FIG. 10 illustrating the slider 400 with the overtube body 320 being omitted, and the sectional view of FIG. 14, the slider 400 moves backward as illustrated in a perspective view of FIG. 25, in a case where the backward movement operation in the sensing zone is performed, in a state where the slider 400 has not reached any of the rear end and the front end of the movable range thereof with respect to the overtube body 320. In this case, the endoscope-coupled member 430 moves backward together with the slider body 402, and as illustrated also in a sectional view of FIG. 27, moves in the downward direction, thereby moving in the direction of the endoscope insertion axis 306*a*.

As described above, in a case where a large amplitude of forward and backward movement operation (the forward and backward movement operation in the sensing zone) of the treatment tool insertion part 202 is performed, the endoscope insertion part 102 is displaced in the axial direction in an interlocking manner with the treatment tool insertion part 202, and in a case where a small amplitude of forward and backward movement operation (the forward and backward movement operation in the dead zone) of the treatment tool insertion part 202 is performed, the endoscope insertion part 102 is not displaced in the axial direction.

Accordingly, in a case where a surgeon has operated to move the treatment tool insertion part 202 forward and backward in the axial direction, the endoscope insertion part 102 also moves in an interlocking manner forward, backward, upward, downward, rightward, and leftward when a large amplitude of forward and backward movement operation is performed. Thus, the visual field, orientation, and the like of the endoscope 100 can be changed as intended by the surgeon. Additionally, the visual field is always given to pick up an image of the distal end of the treatment tool 200 and consequently, an image that is optimal for treatment is automatically provided. In a case where it is desired to check sites other than a site to be treated, the checking can be performed by moving the treatment tool insertion part 202, and a surgeon can perform operations as desired. Therefore, an assistant (endoscopic technician) who operates the endoscope 100 apart from the surgeon can be made unnecessary, and a troublesome condition in which the surgeon should instruct an assistant about the visual field, orientation, and the like of the endoscope 100 serially can be eliminated.

Additionally, when a small amplitude of forward and backward movement operation of the treatment tool insertion part 202 has been performed, the endoscope insertion part 102 does not interlock. Therefore, the size of an object to be observed within an observation image can be prevented from fluctuating unnecessarily, a sense of perspective can be suitably maintained, and a stable observation image can be provided.

Moreover, the endoscope insertion passage 306 of the overtube 300 is oblique to the treatment tool insertion passage 308 and a visual field direction of the endoscope 100 becomes the oblique direction with respect to a forward-backward movement direction of the treatment tool insertion part 202. Thus, when the treatment part 206 of the treatment tool 200 approaches a living body tissue within a body cavity, dead areas are not easily generated by portions other than the distal end of the treatment part 206, it is possible to easily check the state of the distal end of the treatment part 206 while suitably maintaining a sense of perspective, and operability can be improved.

In addition, the sleeve 460 is rotatable with respect to the slider body 402 around its axis. Therefore, in a case where the treatment tool insertion part 202 has been operated to rotate around its axis, the treatment tool insertion part 202 can also be rotated around its axis together with the sleeve 460 without rotating the slider body 402 (without changing the positional relationship (position within the body cavity) of the endoscope insertion part 102 and the treatment tool insertion part 202 with respect to the overtube 300).

Next, an example of the forward and backward movement operation of the endoscope 100 (endoscope insertion part 102) and the treatment tool 200 (treatment tool insertion part 202) in the endoscopic surgical device 10 of the present embodiment will be described.

FIGS. 28A to 29C are explanatory views illustrating the aspect of the operation when treatment of a diseased site within a patient's body cavity is performed using the endoscopic surgical device 10 of the present embodiment, FIGS. 28A to 28C illustrate an aspect of the operation (the forward and backward movement operation in the dead zone) when only the treatment tool 200 moves forward and backward, and FIGS. 29A to 29C illustrate an aspect of the operation (forward and backward movement operation in the sensing zone) when the treatment tool 200 moves forward and backward in an interlocking manner with the endoscope 100.

As illustrated in FIG. 29A, the endoscope 100 (endoscope insertion part 102) and the treatment tool 200 (treatment tool insertion part 202) are respectively inserted into the endoscope insertion passage 306 and the treatment tool insertion passage 308 of the overtube 300 after the overtube 300 is inserted into a patient's body wall and a pneumoperitoneum gas is injected into a body cavity. In this case, the endoscope 100 is coupled to the endoscope-coupled member 430 of the slider 400, and the treatment tool 200 is coupled to the sleeve 460 of the slider 400. Therefore, when the sleeve 460 moves forward and backward within the movable range thereof with respect to the slider body 402, the interlocking is performed with the dead zone (play) where the endoscope 100 does not interlock with the forward and backward movement of the treatment tool 200.

In this state, if the surgeon grips the operating part 204 of the treatment tool 200 and minutely moves the treatment tool 200 forward, only the treatment tool 200 moves forward in a state where the endoscope 100 is stationary as illustrated in FIG. 28B, with respect to the forward movement in the dead zone until the sleeve 460 of the slider 400 abuts against the front end of the movable range thereof.

Similarly, if the surgeon grips the operating part 204 of the treatment tool 200 and minutely moves the treatment tool 200 backward, only the treatment tool 200 moves backward in a state where the endoscope 100 is stationary as illustrated in FIG. 28C, with respect to the backward movement in the dead zone until the sleeve 460 of the slider 400 abuts against the rear end of the movable range thereof.

Therefore, since the endoscope 100 does not move forward and backward with respect to the minute forward and backward movement operation of the treatment tool 200, that is, the forward and backward movement operation thereof in the dead zone, the range of an observation image displayed on the monitor 112 does not change, the size of an object to be observed can be prevented from fluctuating according to the minute displacement of the treatment tool 200, a sense of perspective can be suitably maintained, and a stable observation image can be obtained.

FIG. 29A illustrates that the overtube 300, the endoscope 100, and the treatment tool 200 are in the same state as those of FIG. 28A.

In this state, if the surgeon grips the operating part 204 of the treatment tool 200 and greatly moves the treatment tool 200 forward, the endoscope 100 moves forward in an interlocking manner with the forward movement of the treatment tool 200 through an interlocking function of the slider 400 as illustrated in FIG. 29B, after the forward movement in the dead zone until the sleeve 460 of the slider 400 abuts against the front end of the movable range.

Similarly, if the surgeon grips the operating part 204 of the treatment tool 200 and greatly moves the treatment tool 200 backward, the endoscope 100 moves backward in an interlocking manner with the backward movement of the treatment tool 200 through an interlocking function of the slider 400 as illustrated in FIG. 29C, after the backward movement in the dead zone until the sleeve 460 of the slider 400 abuts against the rear end of the movable range.

Therefore, since the endoscope 100 moves forward and backward with respect to a large forward and backward movement operation of the treatment tool 200, that is, the forward and backward movement operation thereof in the sensing zone, the range of an observation image displayed on the monitor 112 is continuously changed so as to follow the forward and backward movement of the treatment tool 200. Accordingly, since the size of an object to be observed changes according to the operation of the treatment tool 200, an image desired by a surgeon can be simply obtained.

Next, another embodiment of the slider 400 in the overtube 300 will be described. In addition, the embodiment of the above slider 400 is referred to as the first embodiment.

FIGS. 30A to 30C are a horizontal sectional view schematically illustrating the configuration of the slider 400 of a second embodiment, a back view illustrating the configuration from a rear side, and a left side view illustrating the configuration from a left side. In addition, constituent elements having the same or similar functions as those of the constituent elements illustrated in FIGS. 11 to 14, and the like will be designated by the same reference signs, and the description will be omitted.

In the slider 400 of the first embodiment illustrated in FIGS. 11 to 14, and the like, the dead zone where the endoscope insertion part 102 does not interlock with to the forward and backward movement of the treatment tool insertion part 202 is provided by coupling the sleeve 460 to the treatment tool insertion part 202 and by arranging the sleeve 460 so as to be movable in the forward-backward direction with respect to the slider body 402. However, in the second embodiment, the same dead zone is provided by making the endoscope-coupled member 430 coupled to the endoscope insertion part 102 movable not only in the upward-downward direction but also in the forward-backward direction with respect to the slider body 402.

As illustrated in FIGS. 30A to 30C, the slider 400 of the second embodiment has the slider body 402, and the endoscope-coupled member 430 having the same configuration as that of that first embodiment.

The slider body 402 is supported by the same support mechanism as that of the first embodiment so as to be movable in the forward-backward direction inside the overtube body 320. That is, the upper surface and the lower surface of the slider body 402 are provided with the protruding strips 408 and 410 that extend in the direction of the reference axis 300a (treatment tool insertion axis 308a) (refer to FIG. 30B). The protruding strips 408 and 410 are fitted into the guide grooves 370 and 372 that are formed by the respective gaps between the guide plates 374 and 374 and the guide plates 376 and 376 arranged within the overtube body 320, and extend in the direction of reference axis 300a. Accordingly, the slider body 402 is supported so as to be movable in the forward-backward direction within the overtube body 320.

Additionally, the slider body 402 is provided with a through-hole 500 that penetrates in the forward-backward direction, with the treatment tool insertion axis 308a as a central axis. The through-hole 500 has at least a greater diameter than the external diameter of the treatment tool insertion part 202, and forms a portion of the treatment tool insertion passage 308 through which the treatment tool insertion part is inserted.

A cylindrical pressure-contact member (not illustrated) anchored to the slider body 402 is provided inside the through-hole 500, and the treatment tool insertion part 202 and the slider body 402 are coupled (engaged) together via the pressure-contact member by the pressure-contact member being brought into pressure contact with the treatment tool insertion part 202 inserted through the through-hole 500.

Similar to the first embodiment, the endoscope-coupled member 430 is supported so as to be movable in the direction of the endoscope insertion axis 306a, which becomes the oblique direction with respect to the reference axis 300a, by the guide plates 380 and 382 (refer to FIG. 30B) arranged within the overtube body 320, and is coupled (engaged) with the endoscope insertion part 102 inserted through the endoscope insertion passage 306.

Meanwhile, the flat guide surface 440a of the guide part 440 of the endoscope-coupled member 430 is arranged so as to contact or approach a flat left side surface 502 of the slider body 402. The left side surface 502 of the slider body 402 is not provided with the groove 490 (the groove that allows the guide part 440 of the endoscope-coupled member 430 to be fitted thereinto and extends in the upward-downward direction; refer to FIG. 13 and the like) that restricts the movement, in the forward-backward direction, of the endoscope-coupled member 430 with respect to the slider body 402 unlike first embodiment, and the endoscope-coupled member 430 is movable not only in the upward-downward direction but also in the forward-backward direction with respect to the slider body 402. A rear end and a front end of the left side surface 502 of the slider body 402 are provided with protrusions 504 and 506 that protrude in a direction orthogonal to the left side surface 502 from the left side surface 502, and the movable range, in the forward-backward direction, of the endoscope-coupled member 430 with respect to the slider body 402 is limited by the guide part 440 of the endoscope-coupled member 430 abutting against the protrusions 504 and 506.

According to the slider 400 of this second embodiment, the endoscope insertion part 102 inserted through the endoscope insertion passage 306 of the overtube 300 is coupled to the endoscope-coupled member 430, and the treatment tool insertion part 202 inserted through the treatment tool insertion passage 308 of the overtube 300 is coupled to the slider body 402.

Then, supposing that the treatment tool insertion part 202 has been operated to move forward and backward in the forward-backward direction in a state where the endoscope-coupled member 430 does not abut against any of the protrusions 504 and 506 of the slider body 402, while the endoscope-coupled member 430 does not reach any of the protrusions 504 and 506 of the slider body 402, only the slider body 402 moves forward and backward with respect to the overtube body 320 in an interlocking manner with the treatment tool insertion part 202, and the endoscope-coupled member 430 does not move.

Therefore, the dead zone where the endoscope insertion part 102 does not interlock with a small amplitude of forward and backward movement operation of the treatment tool insertion part 202 is provided.

Meanwhile, in a case where the treatment tool insertion part 202 has been operated to move forward in a state where the endoscope-coupled member 430 abuts against the rear protrusion 504 of the slider body 402, or in a case where the treatment tool insertion part 202 has been operated to move backward in a state where the endoscope-coupled member 430 abuts against the front protrusion 506 of the slider body 402, the slider body 402 and the endoscope-coupled member 430 move forward and backward with respect to the overtube body 320 together with the treatment tool insertion part 202. In this case, the endoscope-coupled member 430 moves not only in the forward-backward direction but also in the upward-downward direction together with the slider body 402, and moves in the direction of the endoscope insertion axis 306a.

Therefore, the endoscope insertion part 102 interlocks with a large amplitude of forward and backward movement operation of the treatment tool insertion part 202, and the sensing zone where the endoscope insertion part 102 moves forward and backward in the direction of the endoscope insertion axis 306a that is oblique to the reference axis 300a (treatment tool insertion axis 308a) is provided.

From above, in the slider 400 of the second embodiment, the sleeve 460 in the first embodiment that is coupled to the treatment tool insertion part 202 becomes unnecessary. Therefore, the number of parts can be reduced, it is advantageous to reduction in diameter, and manufacturing costs can also be reduced.

FIGS. 31A to 31C are a horizontal sectional view schematically illustrating the configuration of the slider 400 of a third embodiment, a back view illustrating the configuration from a rear side, and a left side view illustrating the configuration from a left side. In addition, constituent elements having the same or similar functions as those of the constituent elements illustrated in FIGS. 11 to 14, and the like will be designated by the same reference signs, and the description thereof will be omitted.

The slider 400 of the third embodiment is a form in which an operation equivalent to the movement, in the upward-downward direction, of the endoscope-coupled member 430 in the first embodiment is performed by the rotation of the slider 400.

As illustrated in FIGS. 31A to 31C, the slider 400 of the third embodiment has the slider body 402, a first sleeve 520 and a second sleeve 530 that are housed inside the slider body 402.

The slider body 402, when a substantially central portion (a neck portion) thereof in the leftward-rightward direction is divided into left and right, consists of a left body part 540 on the left side arranged at the position of the endoscope insertion axis 306a, and a right body part 542 on the right side arranged at the position of the treatment tool insertion axis 308a.

The right body part 542 has an outer peripheral surface with a shape along a column surface having the treatment tool insertion axis 308a as a central axis, and contacts or approaches guide surfaces 550a and 552a of guide plates 550 and 552 of which upper side and lower sides of outer peripheral surfaces are arranged within the overtube body 320 (refer to of FIG. 31B). The guide plates 550 and 552 extend in the direction of the reference axis 300a within the overtube body 320, and the guide surfaces 550a and 552a are curved so as to correspond to the shape of an outer peripheral surface of the right body part 542.

Accordingly, the slider body 402 is restricted in the movement in the upward-downward direction and in the leftward-rightward directions within the overtube body 320, is supported so as to be movable in the forward-backward direction, and is supported so as to be rotatable around the treatment tool insertion axis 308a.

Additionally, the right body part 542 is provided with a guide part 560 that houses the first sleeve 520 so as to be movable in the forward-backward direction and rotatable around the central axis. In addition, the movement of the first sleeve 520 in the upward-downward direction and in the leftward and rightward direction is restricted. The first sleeve 520 is configured similar to the sleeve 460 of the first embodiment, has a pressure-contact member engaged with the treatment tool insertion part 202, and has a central axis arranged coaxially with the treatment tool insertion axis 308a.

Insertion holes 562a and 564a with a size such that the treatment tool insertion part 202 is insertable therethrough with the position of the treatment tool insertion axis 308a as a central axis are formed at a rear end 562 and a front end 564 of the right body part 542. Therefore, in the slider 400 of the present embodiment, a treatment-tool-side insertion hole through which the treatment tool insertion part 202 is insertable is provided in the right body part 542, and the first sleeve 520 (the pressure-contact member of the first sleeve 520) that is one form of the treatment tool engagement part is held by the treatment-tool-side insertion hole so as to be movable in the forward-backward direction and rotatable.

Accordingly, if the treatment tool insertion part 202 is inserted through the treatment tool insertion passage 308 of the overtube 300, the treatment tool insertion part 202 is inserted through the treatment-tool-side insertion hole of the slider 400, that is, through the guide part 560 and the insertion holes 562a and 564a of the right body part 542 of the slider body 402, and is inserted through the first sleeve 520 and coupled (engaged) with the first sleeve 520. Therefore, the treatment tool-coupled part coupled with the treatment tool insertion part 202 is formed in the right body part 542 of the slider body 402.

The left body part 540 of the slider body 402 is formed integrally with the right body part 542, and is arranged between the guide plates 380 and 382 arranged in the direction of the endoscope insertion axis 306a, which is oblique to the reference axis 300a, within the overtube body 320, similar to the first embodiment. An upper side and a lower side of an outer peripheral surface of the left body part 540 contact or approach the guide plates 380 and 382.

Accordingly, the left body part 540 are moved in the upward-downward direction by the guide plates 380 and 382 with the movement thereof in the forward-backward direction, and moves in the direction of the endoscope insertion axis 306a that is oblique to the reference axis 300a. In this case, the movement of the left body part 540 in the upward-downward direction is performed by the rotation of the slider body 402 (slider 400) around the treatment tool insertion axis 308a.

Meanwhile, the left body part 540 of the slider body 402 is provided with a housing part 570 that houses the second sleeve 530 at a location through which the endoscope insertion axis 306a is inserted. The second sleeve 530 is configured similar to the sleeve 460 of the first embodiment, has a pressure-contact member engaged with the endoscope insertion part 102, and is housed by the housing part 570 so as to be movable in a radial direction (a direction perpendicular to the treatment tool insertion axis 308a; hereinafter simply referred to as a radial direction) with respect to the treatment tool insertion axis 308a that becomes the central axis of the treatment tool insertion part 202 inserted through the treatment-tool-side insertion hole of the right body part 542 so that a central axis thereof is arranged coaxially with the treatment tool insertion axis 306a. Additionally, the second sleeve 530 is held by the housing part 570 so as to be rotatable around its central axis. However, the movement of the second sleeve 530 in the forward-backward direction is restricted.

Additionally, elongated holes 572a and 574a that communicate with the housing part 570 and have a size allowing the endoscope insertion part 102 to be inserted therethrough at the insertion position of the endoscope insertion part 102 are formed at a rear end 572 and a front end 574 of the left body part 540 so as to penetrate in the forward-backward direction. Therefore, in the slider 400 of the present embodiment, the left body part 540 is provided with an endoscope-side insertion hole that allows the endoscope insertion part 102 to be inserted therethrough and consists of an elongated hole that extends in the radial direction. The second sleeve 530 (the pressure-contact member of the second sleeve 530) that is one form of the endoscope engagement part is held by the endoscope-side insertion hole so as to be rotatable, and movable in the radial direction.

Accordingly, if the endoscope insertion part 102 is inserted through the endoscope insertion passage 306 of the overtube 300, the endoscope insertion part 102 is inserted through the endoscope-side insertion hole of the slider 400, that is, through the housing part 570 and the elongated holes 572a and 574a of the left body part 540 of the slider body 402, is inserted through the second sleeve 530, and is coupled (engaged) with of the second sleeve 530. Therefore, the left body part 540 of the slider body 402 is provided with the endoscope-coupled part coupled with the endoscope insertion part 102.

Here, if the slider body 402 moves in the forward-backward direction, the slider body 402 rotates around the treatment tool insertion axis 308a, and the left body part 540 moves in the upward-downward direction, the insertion position of the endoscope insertion part 102 (endoscope insertion axis 306a) with respect to the left body part 540 minutely changes in the radial direction (refer to FIG. 31B). Thus, the elongated holes 572a and 574a that are long in the radial direction are formed at the rear end 572 and the front end 574 of the left body part 540 so that the endoscope insertion part 102 inserted through the endoscope insertion passage 306 is inserted through the left body part 540 at an arbitrary position of the slider body 402 in the forward-backward direction, and the second sleeve 530 is made to be displaceable in the radial direction within the housing part 570. Accordingly, the slider 400 is provided with an adjusting mechanism that adjusts the position of the endoscope engagement part in the radial direction, that is, the distance between the endoscope engagement part and the treatment tool engagement part.

According to the third embodiment of the slider 400, the endoscope insertion part 102 inserted through the endoscope insertion passage 306 of the overtube 300 is coupled to the second sleeve 530, and the treatment tool insertion part 202 inserted through the treatment tool insertion passage 308 of the overtube 300 is coupled to the first sleeve 520.

Then, supposing the treatment tool insertion part 202 has been operated to move forward and backward in the forward-backward direction in a state where the first sleeve 520 does not abut against any of the rear end 562 and the front end 564 of the guide part 560 in the right body part 542 of the slider body 402, while the first sleeve 520 does not reach any of the rear end 562 and the front end 564, only the first sleeve 520 moves forward and backward with respect to the overtube body 320 in an interlocking manner with the treatment tool insertion part 202, and the slider body 402 and the second sleeve 530 do not move.

Therefore, the dead zone where the endoscope insertion part 102 does not interlock with a small amplitude of forward and backward movement operation of the treatment tool insertion part 202 is provided.

Meanwhile, in a case where the treatment tool insertion part 202 has been operated to move forward in a state where the first sleeve 520 abuts against the front end 564 of the slider body 402, or in a case where the treatment tool insertion part 202 has been operated to move backward in a state where the first sleeve 520 abuts against the rear end 562 of the slider body 402, the slider body 402 and the second sleeve 530 move forward and backward with respect to the overtube body 320 together with the treatment tool insertion part 202. In this case, the second sleeve 530 (the pressure-contact member of the second sleeve 530) equivalent to the endoscope engagement part provided in the left body part 540 of the slider body 402 moves not only in the forward-backward direction but also in the upward-downward direction together with the slider body 402, and moves also in the radial direction, and the second sleeve 530 moves in the direction of the endoscope insertion axis 306a.

Therefore, the endoscope insertion part 102 interlocks with a large amplitude of forward and backward movement operation of the treatment tool insertion part 202, and the sensing zone where the endoscope insertion part 102 moves forward and backward in the direction of the endoscope insertion axis 306a that is oblique to the reference axis 300a (treatment tool insertion axis 308a) is provided.

In addition, it is also possible to replace the configurations of the left body part 540 and the right body part 542 of the above slider 400 with each other, thereby adopting a configuration of the treatment tool-coupled part coupled with the treatment tool insertion part 202 as the configuration of the left body part 540, and adopting the configuration of the endoscope-coupled part coupled with the endoscope insertion part 102 as the configuration of the right body part 542.

As described above, in the overtube 300 of each of the above embodiments, a form in which the treatment tool insertion axis 308a that is the central axis of the treatment tool insertion passage 308 is parallel to the reference axis 300a of the overtube 300, and the endoscope insertion axis 306a that is the central axis of the endoscope insertion passage 306 is oblique to (is not parallel to) the reference axis 300a is illustrated. However, the invention is not limited to this, the endoscope insertion passage 306, the treatment tool insertion passage 308, and the slider 400 may be configured so that the endoscope insertion axis 306a is parallel to the reference axis 300a and the treatment tool insertion axis 308a is oblique to reference axis 300a. That is, a configuration may be provided in which the distal end of the endoscope insertion part 102 and the distal end of the treatment tool insertion part 202 delivered from the distal end of the overtube 300 are move forward toward directions away relative to each other by providing the endoscope insertion passage 306 and the treatment tool insertion passage 308 so that at least one of the endoscope insertion axis 306a and the treatment tool insertion axis 308a becomes oblique to the reference axis 300a and so that the endoscope insertion axis 306a and the treatment tool insertion axis 308a become oblique to each other. In this case, if the endoscope insertion axis 306a is oblique to the reference axis 300a, the endoscope-coupled part coupled with the endoscope insertion part 102 in the slider 400 may be provided so as to be slidable in the direction perpendicular to the reference axis 300a, and if the treatment tool insertion axis 308a is oblique to the reference axis 300a, the treatment tool-coupled part coupled with the treatment tool insertion part 202 in the slider 400 may be provided so as to be slidable in the direction perpendicular to the reference axis 300a.

Although the endoscopic surgical device and the overtube related to the invention have been described above in detail, the invention is not limited to the above embodiments, and various improvements and modifications may be made without departing from the concept of the invention.

EXPLANATION OF REFERENCES

10: endoscopic surgical device
100: endoscope
102: endoscope insertion part
104: cable part
108: processor device
110: light source device
112: monitor
114, 304: distal end surface
116: observation window
118: illumination window
200: treatment tool
202: treatment tool insertion part
204: operating part
206: treatment part
208: sheath
210: fixed handle
214: movable handle
300: overtube
300a: reference axis
302: base end surface
306: endoscope insertion passage
306a: endoscope insertion axis
308: treatment tool insertion passage
308a: treatment tool insertion axis
310: endoscope insertion port
312: endoscope delivery port
314: treatment tool insertion port
316: treatment tool delivery port
320: overtube body
322: outer wall
324: cavity part
340: base end cap
360: distal end cap
370, 372: guide groove
374, 376, 380, 382, 550, 552: guide plate
400: slider
402: slider body
408, 410: protruding strip
420, 540: endoscope-coupled part
422, 542: treatment tool-coupled part
430: endoscope-coupled member
432: frame body
434, 466: pressure-contact member
440, 480, 560, 570: guide part
460: sleeve
464: sleeve body
490: groove

What is claimed is:

1. An endoscopic surgical device comprising:
an endoscope including an endoscope insertion part having an observation part provided at a distal end thereof;
a treatment tool including a treatment tool insertion part having a treatment part provided at a distal end thereof; and
an overtube that guides the endoscope insertion part and the treatment tool insertion part into a body cavity,
wherein the overtube includes
an overtube body that passes through a body wall and is inserted into the body cavity,
an endoscope insertion passage that is provided inside the overtube body and allows the endoscope insertion part to be inserted therethrough so as to be movable forward and backward,
a treatment tool insertion passage that is provided inside the overtube body and allows the treatment tool insertion part to be inserted therethrough so as to be movable forward and backward, and
a slider that includes an endoscope engagement part holding the endoscope insertion part that is inserted through the endoscope insertion passage, and a treatment tool engagement part holding the treatment tool insertion part that is inserted through the treatment tool insertion passage, the slider being arranged inside the overtube body so as to be movable forward and backward relative to the overtube body in an axial direction of the overtube body, wherein an axial direction of the endoscope insertion passage is in an oblique direction with respect to an axial direction of the treatment tool insertion passage, and the axial direction of the endoscope insertion passage crosses the axial direction of the treatment tool insertion passage when viewed from a direction perpendicular to both the axial direction of the endoscope insertion passage and the treatment tool insertion passage, and the slider is capable of adjusting a distance in a direction perpendicular to the axial direction of the overtube body between the endoscope engagement part and the treatment tool engagement part according to a position of the slider in the axial direction of the overtube body.

2. The endoscopic surgical device according to claim 1, wherein the axial direction of the endoscope insertion passage is provided obliquely to the axial direction of the overtube body.

3. The endoscopic surgical device according to claim 2, wherein the axial direction of the treatment tool insertion passage is provided parallel to the axial direction of the overtube body.

4. The endoscopic surgical device according to claim 1, wherein the slider causes any one of the endoscope engagement part and the treatment tool engagement part to slide in a direction having a movement component perpendicular to the axial direction of the overtube body with respect to the other engagement part, along with the forward and backward movement of the endoscope insertion part or the treatment tool insertion part.

5. The endoscopic surgical device according to claim 4, wherein the slider includes a guide projection that is provided in any one of the endoscope engagement part and the treatment tool engagement part, and a guide groove that is provided in the other of the endoscope engagement part and the treatment tool engagement part and causes the guide projection to slide in a direction having a movement component perpendicular to the axial direction of the overtube body.

6. The endoscopic surgical device according to claim 1, wherein the slider is provided so as to be rotatable with respect to the longitudinal axis of the overtube body, the slider further comprises:

an endoscope-side insertion hole that is provided in the slider and rotatably holds the endoscope engagement part, and a treatment-tool-side insertion hole that is provided in the slider, and rotatably holds the treatment tool engagement part, and wherein any one insertion hole of the endoscope-side insertion hole and the treatment-tool-side insertion hole includes an elongated hole that extends in a direction perpendicular to the longitudinal axis of the endoscope insertion part or the treatment tool insertion part inserted through the other insertion hole.

7. The endoscopic surgical device according to claim 1, wherein the slider has a first stopper and a second stopper separated from each other in the axial direction of the overtube body, and one of the endoscope engagement part and the treatment tool engagement part is movable between the first stopper and the second stopper, the other one of the endoscope engagement part and the treatment tool engagement part is fixed with respect to the slider.

8. An overtube that guides an endoscope including an endoscope insertion part having an observation part provided at a distal end thereof, and a treatment tool including a treatment tool insertion part having a treatment part provided at a distal end thereof into a body cavity, the overtube comprising:

an overtube body that passes through a body wall and is inserted into the body cavity;

an endoscope insertion passage that is provided inside the overtube body and allows the endoscope insertion part to be inserted therethrough so as to be movable forward and backward;

a treatment tool insertion passage that is provided inside the overtube body and allows the treatment tool insertion part to be inserted therethrough so as to be movable forward and backward, and a slider that includes an endoscope engagement part holding the endoscope insertion part that is inserted through the endoscope insertion passage, and a treatment tool engagement part holding the treatment tool insertion part that is inserted through the treatment tool insertion passage, the slider being arranged inside the overtube body so as to be movable forward and backward relative to the overtube body in an axial direction of the overtube body, wherein an axial direction of the endoscope insertion passage is in an oblique direction with respect to an axial direction of the treatment tool insertion passage, and the axial direction of the endoscope insertion passage crosses the axial direction of the treatment tool insertion passage when viewed from a direction perpendicular to the axial direction of the endoscope insertion passage and the treatment tool insertion passage, the slider is capable of adjusting a distance in a direction perpendicular to the axial direction of the overtube body between the endoscope engagement part and the treatment tool engagement part according to a position of the slider in the axial direction of the overtube body.

9. The overtube according to claim 8, wherein the axial direction of the endoscope insertion passage is provided obliquely to the axial direction of the overtube body.

10. The overtube according to claim 9, wherein the axial direction of the treatment tool insertion passage is provided parallel to the axial direction of the overtube body.

11. The overtube according to claim 8, wherein the slider causes any one of the endoscope engagement part and the treatment tool engagement part to slide in a direction having a movement component perpendicular to the axial direction of the overtube body with respect to the other engagement part, along with the forward and backward movement of the endoscope insertion part or the treatment tool insertion part.

12. The overtube according to claim 11, wherein the slider includes a guide projection that is provided in any one of the endoscope engagement part and the treatment tool engagement part, and a guide groove that is provided in the other of the endoscope engagement part and the treatment tool engagement part and causes the guide projection to slide in a direction having a movement component perpendicular to the axial direction of the overtube body.

13. The overtube according to claim 8,
wherein the slider is provided so as to be rotatable with respect to the longitudinal axis of the overtube body,
the slider further comprises:
an endoscope-side insertion hole that is provided in the slider and rotatably holds the endoscope engagement part, and
a treatment-tool-side insertion hole that is provided in the slider, and rotatably holds the treatment tool engagement part, and
wherein any one insertion hole of the endoscope-side insertion hole and the treatment-tool-side insertion hole includes an elongated hole that extends in a direction perpendicular to the longitudinal axis of the endoscope insertion part or the treatment tool insertion part inserted through the other insertion hole.

14. The overtube according to claim 8,
wherein the slider has a first stopper and a second stopper separated from each other in the axial direction of the overtube body, and
one of the endoscope engagement part and the treatment tool engagement part is movable between the first stopper and the second stopper, the other one of the endoscope engagement part and the treatment tool engagement part is fixed with respect to the slider.

* * * * *